(12) United States Patent
Garber et al.

(10) Patent No.: US 11,977,134 B2
(45) Date of Patent: May 7, 2024

(54) MITIGATION OF AN EFFECT OF CAPACITIVELY COUPLED CURRENT WHILE DRIVING A SENSOR COMPONENT OVER AN UNSHIELDED TWISTED PAIR WIRE CONFIGURATION

(71) Applicant: HI LLC, Los Angeles, CA (US)

(72) Inventors: Stephen Garber, Santa Monica, CA (US); Hooman Mohseni, Wilmette, IL (US)

(73) Assignee: HI LLC, Los Angeles, CA (US)

( * ) Notice: Subject to any disclaimer, the term of this patent is extended or adjusted under 35 U.S.C. 154(b) by 630 days.

(21) Appl. No.: 17/161,840

(22) Filed: Jan. 29, 2021

(65) Prior Publication Data
US 2021/0263115 A1 Aug. 26, 2021

Related U.S. Application Data

(60) Provisional application No. 63/125,660, filed on Dec. 15, 2020, provisional application No. 62/980,863, filed on Feb. 24, 2020.

(51) Int. Cl.
*G01R 33/00* (2006.01)
*A61B 5/242* (2021.01)
(Continued)

(52) U.S. Cl.
CPC .......... *G01R 33/0076* (2013.01); *A61B 5/242* (2021.01); *H01B 11/04* (2013.01);
(Continued)

(58) Field of Classification Search
CPC ............ G01R 33/0076; G01R 33/0094; G01R 33/0017; G01R 33/025; G01R 33/0035;
(Continued)

(56) References Cited

U.S. PATENT DOCUMENTS 3,173,082 A 3/1965 Bell et al.
3,257,608 A 6/1966 Bell et al.
(Continued)

FOREIGN PATENT DOCUMENTS

CN 104730484 6/2015
CN 107562188 1/2018
(Continued)

OTHER PUBLICATIONS

Capocci, Romano, et al. "Inspection-class remotely operated vehicles—A review." Journal of Marine Science and Engineering 5.1 (2017): 13. (Year: 2017).*

(Continued)

*Primary Examiner* — Christopher P Mcandrew
(74) *Attorney, Agent, or Firm* — ALG Intellectual Property, LLC

(57) ABSTRACT

An illustrative system includes a sensor component and a controller conductively coupled by way of a first wire and a second wire in a twisted pair configuration. The controller includes a driver configured to drive the sensor component by way of the first and second wires with a drive current in accordance with a gain parameter and a control loop circuit. The control loop circuit is configured to receive a control signal representative of a target current value for the drive current, adjust the gain parameter based on a difference between the target current value and an actual current value of current that is actually being driven through the sensor component, and abstain from adjusting the gain parameter based on current capacitively coupled onto the first and second wires by an external electric field.

22 Claims, 15 Drawing Sheets

(51) Int. Cl.
*A61B 5/245* (2021.01)
*H01B 11/04* (2006.01)

(52) U.S. Cl.
CPC ....... *A61B 5/245* (2021.01); *A61B 2562/0223* (2013.01); *A61B 2562/18* (2013.01)

(58) Field of Classification Search
CPC ....... A61B 5/242; A61B 5/4064; A61B 5/245; A61B 2562/022; A61B 2562/18; A61B 5/6803; H01B 11/04
USPC .......................................................... 324/260
See application file for complete search history.

(56) References Cited

U.S. PATENT DOCUMENTS

| | | | |
|---|---|---|---|
| 3,495,161 A | 2/1970 | Bell | |
| 3,501,689 A | 3/1970 | Robbiano | |
| 3,513,381 A | 5/1970 | Happer, Jr. | |
| 4,193,029 A | 3/1980 | Cioccio et al. | |
| 4,951,674 A | 8/1990 | Zanakis et al. | |
| 5,189,368 A | 2/1993 | Chase | |
| 5,192,921 A | 3/1993 | Chantry et al. | |
| 5,225,778 A | 7/1993 | Chaillout et al. | |
| 5,254,947 A | 10/1993 | Chaillout et al. | |
| 5,309,095 A | 5/1994 | Ahonen et al. | |
| 5,442,289 A | 8/1995 | Dilorio et al. | |
| 5,444,372 A * | 8/1995 | Wikswo, Jr. | G01R 33/0358 324/262 |
| 5,471,985 A | 12/1995 | Warden | |
| 5,506,200 A | 4/1996 | Hirschkoff et al. | |
| 5,526,811 A | 6/1996 | Lypchuk | |
| 5,713,354 A | 2/1998 | Warden | |
| 6,118,070 A * | 9/2000 | Tamura | H01Q 13/20 174/36 |
| 6,144,872 A | 11/2000 | Graetz | |
| 6,339,328 B1 * | 1/2002 | Keene | G01R 33/0206 324/225 |
| 6,472,869 B1 | 10/2002 | Upschulte et al. | |
| 6,546,100 B1 * | 4/2003 | Drew | H03H 7/427 379/415 |
| 6,593,884 B1 * | 7/2003 | Gilboa | A61B 5/062 342/450 |
| 6,665,553 B2 | 12/2003 | Kandori et al. | |
| 6,806,784 B2 | 10/2004 | Hollberg et al. | |
| 6,831,522 B2 | 12/2004 | Kitching et al. | |
| 7,038,450 B2 | 5/2006 | Romalis et al. | |
| 7,102,451 B2 | 9/2006 | Happer et al. | |
| 7,145,333 B2 | 12/2006 | Romalis et al. | |
| 7,521,928 B2 | 4/2009 | Romalis et al. | |
| 7,656,154 B2 | 2/2010 | Kawabata et al. | |
| 7,826,065 B1 | 11/2010 | Okandan et al. | |
| 7,872,473 B2 | 1/2011 | Kitching et al. | |
| 7,994,783 B2 | 8/2011 | Ledbetter et al. | |
| 8,054,074 B2 | 11/2011 | Ichihara et al. | |
| 8,212,556 B1 | 7/2012 | Schwindt et al. | |
| 8,258,884 B2 | 9/2012 | Borwick, III et al. | |
| 8,319,156 B2 | 11/2012 | Borwick, III et al. | |
| 8,334,690 B2 | 12/2012 | Kitching et al. | |
| 8,373,413 B2 | 2/2013 | Sugioka | |
| 8,405,389 B2 | 3/2013 | Sugioka et al. | |
| 8,587,304 B2 | 11/2013 | Budker et al. | |
| 8,836,327 B2 | 9/2014 | French et al. | |
| 8,906,470 B2 | 12/2014 | Overstolz et al. | |
| 8,941,377 B2 | 1/2015 | Mizutani et al. | |
| 9,095,266 B1 | 8/2015 | Fu | |
| 9,116,201 B2 | 8/2015 | Shah et al. | |
| 9,140,590 B2 | 9/2015 | Waters et al. | |
| 9,140,657 B2 | 9/2015 | Ledbetter et al. | |
| 9,169,974 B2 | 10/2015 | Parsa et al. | |
| 9,244,137 B2 | 1/2016 | Kobayashi et al. | |
| 9,291,508 B1 | 3/2016 | Biedermann et al. | |
| 9,343,447 B2 | 3/2016 | Parsa et al. | |
| 9,366,735 B2 | 6/2016 | Kawabata et al. | |
| 9,383,419 B2 | 7/2016 | Mizutani et al. | |
| 9,395,425 B2 | 7/2016 | Diamond et al. | |
| 9,417,293 B2 | 8/2016 | Schaffer et al. | |
| 9,429,918 B2 | 8/2016 | Parsa et al. | |
| 9,568,565 B2 | 2/2017 | Parsa et al. | |
| 9,575,144 B2 | 2/2017 | Kornack et al. | |
| 9,601,225 B2 | 3/2017 | Parsa et al. | |
| 9,638,768 B2 * | 5/2017 | Foley | G01C 19/62 |
| 9,639,062 B2 | 5/2017 | Dyer et al. | |
| 9,677,905 B2 | 6/2017 | Waters et al. | |
| 9,726,626 B2 | 8/2017 | Smith et al. | |
| 9,726,733 B2 | 8/2017 | Smith et al. | |
| 9,791,536 B1 | 10/2017 | Alem et al. | |
| 9,829,544 B2 | 11/2017 | Bulatowicz | |
| 9,846,054 B2 | 12/2017 | Waters et al. | |
| 9,851,418 B2 | 12/2017 | Wolf et al. | |
| 9,869,731 B1 | 1/2018 | Hovde et al. | |
| 9,915,711 B2 | 3/2018 | Kornack et al. | |
| 9,927,501 B2 | 3/2018 | Kim et al. | |
| 9,948,314 B2 | 4/2018 | Dyer et al. | |
| 9,964,609 B2 | 5/2018 | Ichihara et al. | |
| 9,964,610 B2 | 5/2018 | Shah et al. | |
| 9,970,999 B2 | 5/2018 | Larsen et al. | |
| 9,995,800 B1 | 6/2018 | Schwindt et al. | |
| 10,024,929 B2 | 7/2018 | Parsa et al. | |
| 10,088,535 B1 | 10/2018 | Shah | |
| 10,162,016 B2 | 12/2018 | Gabrys et al. | |
| 10,371,764 B2 | 8/2019 | Morales et al. | |
| 10,627,460 B2 | 4/2020 | Alford et al. | |
| 2004/0232912 A1 | 11/2004 | Tsukamoto et al. | |
| 2005/0007118 A1 | 1/2005 | Kitching et al. | |
| 2005/0046851 A1 | 3/2005 | Riley, Jr. et al. | |
| 2005/0206377 A1 * | 9/2005 | Romalis | G01R 33/02 324/301 |
| 2007/0120563 A1 | 5/2007 | Kawabata et al. | |
| 2007/0167723 A1 * | 7/2007 | Park | G01R 33/032 600/409 |
| 2007/0205767 A1 | 9/2007 | Xu et al. | |
| 2009/0079426 A1 | 3/2009 | Anderson | |
| 2009/0101806 A1 | 4/2009 | Masuda | |
| 2010/0219820 A1 | 9/2010 | Skidmore et al. | |
| 2011/0001478 A1 * | 1/2011 | Wemmer | G01R 33/0322 324/309 |
| 2011/0062956 A1 | 3/2011 | Edelstein et al. | |
| 2012/0112749 A1 | 5/2012 | Budker et al. | |
| 2012/0313634 A1 * | 12/2012 | Parks | G01R 33/0322 324/244.1 |
| 2013/0082700 A1 | 4/2013 | Mizutani et al. | |
| 2013/0082701 A1 | 4/2013 | Mizutani et al. | |
| 2013/0120882 A1 * | 5/2013 | Love | H02H 3/33 361/42 |
| 2013/0265042 A1 | 10/2013 | Kawabata et al. | |
| 2014/0306700 A1 * | 10/2014 | Kamada | G01R 33/0322 324/244.1 |
| 2014/0354275 A1 | 12/2014 | Sheng et al. | |
| 2015/0022200 A1 | 1/2015 | Ichihara et al. | |
| 2015/0054504 A1 | 2/2015 | Ichihara et al. | |
| 2015/0378316 A1 | 12/2015 | Parsa et al. | |
| 2016/0061913 A1 | 3/2016 | Kobayashi et al. | |
| 2016/0116553 A1 | 4/2016 | Kim et al. | |
| 2016/0223627 A1 | 8/2016 | Shah et al. | |
| 2016/0313417 A1 | 10/2016 | Kawabata et al. | |
| 2017/0023653 A1 | 1/2017 | Kobayashi et al. | |
| 2017/0023654 A1 | 1/2017 | Kobayashi et al. | |
| 2017/0067969 A1 | 3/2017 | Butters et al. | |
| 2017/0090568 A1 * | 3/2017 | Chen | G06F 3/014 |
| 2017/0199138 A1 | 7/2017 | Parsa et al. | |
| 2017/0261564 A1 | 9/2017 | Gabrys et al. | |
| 2017/0331485 A1 | 11/2017 | Gobet et al. | |
| 2017/0343617 A1 | 11/2017 | Manickam et al. | |
| 2017/0343695 A1 | 11/2017 | Stetson et al. | |
| 2018/0003777 A1 | 1/2018 | Sorenson et al. | |
| 2018/0038921 A1 | 2/2018 | Parsa et al. | |
| 2018/0100749 A1 | 4/2018 | Waters et al. | |
| 2018/0128885 A1 | 5/2018 | Parsa et al. | |
| 2018/0156875 A1 | 6/2018 | Herbsommer et al. | |
| 2018/0219353 A1 | 8/2018 | Shah | |
| 2018/0238974 A1 | 8/2018 | Shah et al. | |
| 2018/0313908 A1 | 11/2018 | Knappe et al. | |
| 2018/0313913 A1 | 11/2018 | Denatale et al. | |

(56) References Cited

U.S. PATENT DOCUMENTS

| | | |
|---|---|---|
| 2019/0391213 A1 | 12/2019 | Alford |
| 2020/0025844 A1 | 1/2020 | Alford et al. |
| 2020/0057115 A1 | 2/2020 | Jiménez-Martínez |
| 2020/0057116 A1 | 2/2020 | Zorzos et al. |
| 2020/0072916 A1 | 3/2020 | Alford |
| 2020/0088811 A1 | 3/2020 | Mohseni |
| 2020/0256929 A1 | 8/2020 | Ledbetter et al. |
| 2020/0309873 A1 | 10/2020 | Ledbetter et al. |
| 2020/0341081 A1 | 10/2020 | Mohseni et al. |
| 2020/0348368 A1* | 11/2020 | Garber ............... G01R 33/0011 |

FOREIGN PATENT DOCUMENTS

| | | |
|---|---|---|
| EP | 2738627 | 6/2014 |
| EP | 2380029 | 10/2015 |
| EP | 3037836 | 9/2017 |
| JP | 2016109665 | 6/2016 |
| JP | 2018004462 | 1/2018 |
| WO | 2005081794 | 9/2005 |
| WO | 2014031985 | 2/2014 |
| WO | 2017095998 | 6/2017 |

OTHER PUBLICATIONS

Barber, M.E. et al., Details of the Dual End Current Source with Active Common-Mode Rejection, Springer Theses; Appendix A; pp. 169-190 (2018).
Alem, O. et al., "Magnetic Field Imaging with Microfabricated Optically-Pumped Magnetometers," Opt. Express 25, 7849-7858 (2017).
Allred, J.C. et al., "High-Sensitivity Atomic Magnetometer Unaffected by Spin-Exchange Relaxation," Physical Review Letters, 89(13), 130801 (2002).
Balabas, et al., "Polarized Alkali Vapor with Minute-Long Transverse Spin-Relaxation Time," Phys. Rev. Lett. 105, 070801 Published Aug. 12, 2010.
Baranga, A.B. et al., "An Atomic Magnetometer for Brain Activity Imaging," Real Time Conference 2005. 14th IEEE-NPSS. pp. 417-418 (2005).
Barbieri, F. et al., "Local Recording of Biological Magnetic Fields Using Giant Magneto Resistance-Based Micro-Probes," Scientific Reports, 6, 39330, Dec. 19, 2016.
Borna, A. et al., "A 20-Channel Magnetoencephalography System Based on Optically Pumped Magnetometers," Physics in Medicine & Biology 62.23 (2017): 8909.
Boto, E. et al., "Moving Magnetoencephalography Towards Real World Applications with a Wearable System," Nature, vol. 555, pp. 657-661 (2018).
Budker, D. et al., "Optical Magnetometry," Nature Physics, 2008, https://arxiv.org/abs/physics/0611246v1.
Colombo, A. et al., "Four-Channel Optically Pumped Atomic Magnetometer for Magnetoencephalography," Opt. Express 24, 15403-15416 (2016).
Dang, H.B. et al., "Ultra-High Sensitivity Magnetic Field and Magnetization Measurements with an Atomic Magnetometer," Applied Physics Letters. 97. 10.1063/1.3491215 (2010).
Dong, H. et al., "Atomic-Signal-Based Zero-Field Finding Technique for Unshielded Atomic Vector Magnetometer," IEEE Sensors Journal, IEEE Service Center, New York, NY, US, vol. 13, No. 1. Jan. 1, 2013 (Jan. 1, 2013), pp. 186-189.
Donley, E.A. et al., "Demonstration of High-Performance Compact Magnetic Shields for Chip-Scale Atomic Devices," The Review of Scientific Instruments. 78. 083102 (2007).
Dupont-Roc, J. et al., "Detection of Very Weak Magnetic Fields (10-9gauss) by 87Rb Zero-Field Level Crossing Resonances," Physics Letters A—Phys Lett A. 28. 638-639 10.1016/0375-9601(69) 90480-0 Feb. 10, 1969.
Fang, J. et al., "In Situ Triaxial Magnetic Field Compensation for the Spin-Exchange-Relaxation-Free Atomic Magnetometer," Review of Scientific Instruments, 83(10), p. 103104 (2012).
Griffith, C. et al., "Miniature Atomic Magnetometer Integrated with Flux Concentrators," Applied Physics Letters—Appl Phys Lett. 94. 10.1063/1.3056152, Jan. 14, 2009.
Hamalainen, M. et al., "Magnetoencephalograph—Theory, Instrumentation, and Applications to Noninvasive Studies of the Working Human Brain," Reviews of Modern Physics, vol. 65, Issue 2. 413-497 (1993).
Hill, R.M. et al., "A Tool for Functional Brain imaging with Lifespan Compliance," Nature Communications (2019) 10:4785. https://doi.org/10.1038/s41467-019-12486-x.
Hill, R.M. et al., "Multi-Channel Whole-Head OPM-MEG: Helmet Design and a Comparison with a Conventional System," NeuroImage vol. 219 (2020) 116995. https://doi.org/10.1016/j.neuroimage.2020.116995.
Hu, Y. et al., "Reduction of Far Off-Resonance Laser Frequency Drifts Based on the Second Harmonic of Electro-Optic Modulator Detection in the Optically Pumped Magnetometer," Applied Optics. 56. 5927. 10.1364/AO.56.005927 Jul. 18, 2017.
Huang, H. et al., "Single-Beam Three-Axis Atomic Magnetometer," Applied Physics Letters 109.6 (2016): 062404. (Year: 2016).
Hunter, D. et al., "Free-Induction-Decay Magnetometer Based on a Microfabricated Cs Vapor Cell," Physical Review Applied (10). ISSN 2331-7019, Jul. 5, 2018.
Ijsselsteijn, R. et al., "A Full Optically Operated Magnetometer Array: An Experimental Study," The Review of Scientific Instruments. 83. 113106. 10.1063/1.4766961, Nov. 27, 2012.
Jackson Kimball, D.F. et al., "Magnetic Shielding and Exotic Spin-Dependent Interactions," Physical Review D. 94. 10.1103/PhysRevD.94.082005, Oct. 21, 2016.
Jimenez-Martinez, R. et al., "Sensitivity Comparison of Mx and Frequency-Modulated Bell-Bloom Cs Magnetometers in a Microfabricated Cell," IEEE Transactions on Instrumentation and Measurement, 59(2), 372-378 Feb. 2010.
Kim, K. et al., "Multi-Channel Atomic Magnetometer for Magnetoencephalography: A Configuration Study," NeuroImage 89 (2014) 143-151 https://physics.princeton.edu/romalis/papers/Kim_2014.pdf.
Kim, Y.J. et al., "Ultra-Sensitive Magnetic Microscopy with an Optically Pumped Magnetometer," Scientific Reports. 6. 24773. 10.1038/srep24773, Apr. 22, 2016.
Knappe, S. et al., "Optically-Pumped Magnetometers for MEG," Springer-Verlag Berlin Heidelberg, 2014; pp. 993-999; DOI: 10.1007/978-3-642-33045-2_49, Aug. 8, 2014.
Kominis, I.K. et al., "A Subfemtotesla Multichannel Atomic Magnetometer," Nature Publishing Group, vol. 422(6932), p. 596-599. Apr. 2003.
Korth, H. et al., "Miniature Atomic Scalar Magnetometer for Space Based on the Rubidium Isotope 87 Rb," J. Geophys. Res. Space Physics, 121, 7870-7880, doi: 10.1002/2016JA022389, Jul. 23, 2016.
Lee, S.K. et al., "Calculation of Magnetic Field Noise from High-Permeability Magnetic Shields and Conducting Objects with Simple Geometry," Journal of Applied Physics. 103. 084904-084904. 10.1063/1.2885711, Apr. 23, 2008.
Lee, H.J. et al., "Flat-Response Spin-Exchange Relaxation Free Atomic Magnetometer Under Negative Feedback," Optics Express. 22. 10.1364/OE.22.019887, Aug. 11, 2014.
Lenz, J. et al., "Magnetic Sensors and Their Applications," IEEE Sensors Journal, 6(3), pp. 631-649, Jun. 2006.
Li, S. et al., "Optical Rotation in Excess of 100 Rad Generated by Rb Vapor in a Multipass Cell," Phys. Rev. A. 84. 10.1103/PhysRevA.84.061403, Dec. 6, 2011.
Lorenz, V.O. et al., "High-Density, High-Temperature Alkali Vapor Cell," Review of Scientific Instruments, 79, 123104, 4 pages, 2008.
Masuda, Y. et al., "3He Polarization via Optical Pumping in a Birefringent Cell," Applied Physics Letters. 87. 10.1063/1.2008370, Jul. 28, 2005.
Maze, J.R. et al., "Nanoscale Magnetic Sensing with an Individual Electronic Spin in Diamond," Nature, 455(7213), 644. Oct. 2008.
Navau, C. et al., "Magnetic Energy Harvesting and Concentration at a Distance by Transformation Optics," Physical Review Letters. 109. 263903. 10.1103/PhysRevLett.109.263903, Dec. 28, 2012.

(56) References Cited

OTHER PUBLICATIONS

Neuman, J.A. et al., "Robust High-Temperature Sapphire Cell for Metal Vapors," Review of Scientific Instruments, vol. 66, Issue 4, Apr. 1995, pp. 3021-3023.

Ryan, L.J. et al., "Miniature Vector Laser Magnetometer Measurements of Earth's Field," May 10, 2004. 4 pgs.

Sander, T.H. et al., "Magnetoencephalography with a Chip-Scale Atomic Magnetometer," Biomed Opt Express. 2012;3(5):981-90.

Schoenmaker, J. et al., "Magnetic Flux Amplification by Lenz Lenses," The Review of Scientific Instruments. 84. 085120. 10.1063/1.4819234, Aug. 30, 2013.

Schultze, V. et al., "An Optically Pumped Magnetometer Working in the Light-Shift Dispersed Mz Mode," Sensors, 2017, 17, 561; doi:10.3390/s17030561.

Seltzer, S.J. et al., "Developments in Alkali-Metal Atomic Magnetometry," Nov. 1, 2008 (Nov. 1, 2008), XP055616618, ISBN: 978-0-549-93355-7. https://physics.princeton.edu/atomic/romalis/papers/Seltzer%20Thesis.pdf. pp. 148-159.

Seltzer, S.J. et al., "High-Temperature Alkali Vapor Cells with Anti-Relaxation Surface Coatings," Journal of Applied Physics. 106. 114905-114905. 10.1063/1.3236649, Dec. 2, 2009.

Seltzer, S.J. et al., "Unshielded Three-Axis Vector Operation of a Spin-Exchange-Relaxation-Free Atomic Magnetometer," Applied Physics Letters 85.20 (2004): 4804-4806.

Sheng, D. et al., "A Microfabricated Optically-Pumped Magnetic Gradiometer," Applied Physics Letters. 110. 10.1063/1.4974349, Jan. 18, 2017.

Sheng, D. et al., "Subfemtotesla Scalar Atomic Magnetometry Using Multipass Cells," Physical Review Letters. 110. 160802. 10.1103/PhysRevLett.110.160802, Apr. 18, 2013.

Slocum, R.E. et al., "Design and Operation of the Miniature Vector Laser Magnetometer," NASA Earth Science Technology Conference 2003 (2003).

Slocum, et al., "Self-Calibrating Vector Magnetometer for Space," https://esto.nasa.gov/conferences/esto-2002/Papers/B3P4(Slocum).pdf (2002).

Tierney, T.M. et al., "Cognitive Neuroscience Using Wearable Magnetometer Arrays: Non-Invasive Assessment of Language Function," NeuroImage vol. 181 (2018) pp. 513-520. https://doi.org/10.1016/j.neuroimage.2018.07.035.

Vovrosh, J. et al., "Additive Manufacturing of Magnetic Shielding and Ultra-High Vacuum Flange for Cold Atom Sensors," Scientific Reports. 8. 10.1038/s41598-018-20352-x, Jan. 31, 2018.

Zetter, R. et al., "Optical Co-registration of MRI and On-scalp MEG," Scientific Reports (2019) 9:5490. https://doi.org/10.1038/s41598-019-41763-4.

\* cited by examiner

MITIGATION OF AN EFFECT OF CAPACITIVELY COUPLED CURRENT WHILE DRIVING A SENSOR COMPONENT OVER AN UNSHIELDED TWISTED PAIR WIRE CONFIGURATION

RELATED APPLICATIONS

The present application claims priority under 35 U.S.C. § 119(e) to U.S. Provisional Patent Application No. 63/125,660, filed on Dec. 15, 2020, and to U.S. Provisional Patent Application No. 62/980,863, filed on Feb. 24, 2020. These applications are incorporated herein by reference in their respective entireties.

BACKGROUND INFORMATION

Sensor systems that rely on electrical signals between a sensing apparatus and system electronics are susceptible to disturbance and performance degradation caused by external electric fields, such as those generated by atmospheric effects, power transmission wiring, and/or fluorescent lighting electronics. In particular, sensor systems that include system electronics that drive current through a remote sensing component by way of wires in a twisted pair configuration can be negatively affected by current that is capacitively coupled onto the wires by external electric fields.

Conventional approaches to mitigating the effects of such current include the use of shielded cables (e.g., coaxial or triaxial cables) that shunt currents injected by external electric fields to a controlled voltage. Unfortunately, these shielded cables are often large, stiff, and heavy, thereby making sensor systems (e.g., magnetoencephalography (MEG) sensor systems used to measure magnetic fields generated by the brain) that utilize shielded cables difficult and costly to use in many applications.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements. Furthermore, the figures are not necessarily drawn to scale as one or more elements shown in the figures may be enlarged or resized to facilitate recognition and discussion.

DETAILED DESCRIPTION

Figure 1:
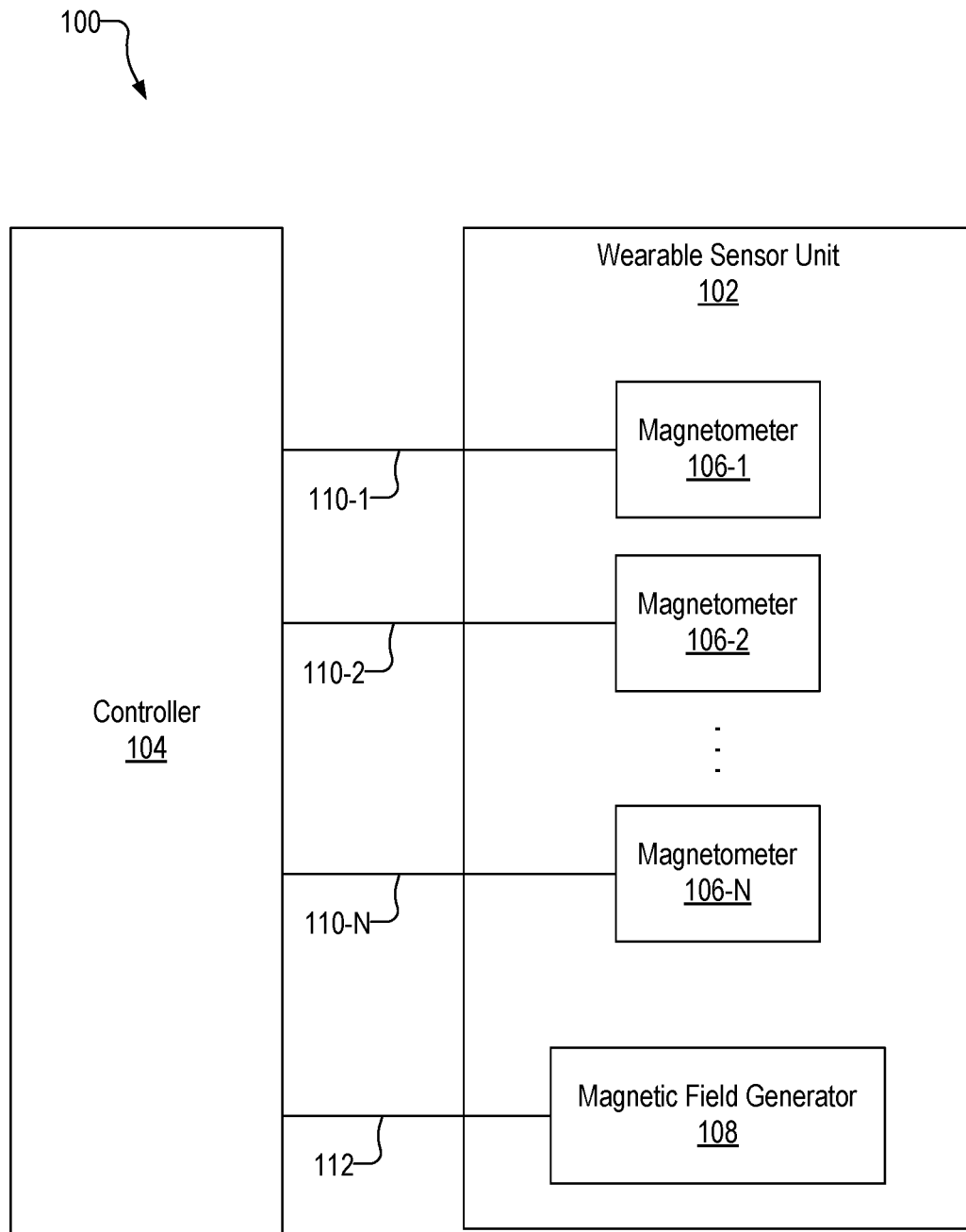
FIG. 1 illustrates an exemplary magnetic field measurement system.

Systems, circuits, and methods for mitigating an effect of capacitively coupled current while a sensor component is driven over an unshielded twisted pair wire configuration are described herein. For example, an illustrative system includes a sensor component and a controller conductively coupled to the sensor component by way of a first wire and a second wire in a twisted pair configuration. The controller includes a driver and a control loop. The driver is configured to drive the sensor component over the first and second wires with a drive current in accordance with a gain parameter. The control loop circuit is configured to receive a control signal representative of a target current value for the drive current and adjust the gain parameter based on a difference between the target current value and an actual current value of current that is actually being driven through the sensor component. This adjustment is configured to reduce the difference between the target current value and the actual current value. The control loop is further configured to abstain from adjusting the gain parameter based on current capacitively coupled onto the first and second wires by an external electric field.

As described herein, the control loop circuit may abstain from adjusting the gain parameter based on the capacitively coupled current by including two current sensors—one for each wire included in the twisted pair configuration. The first current sensor is configured to measure a first actual current value of current that is actually on the first wire while the sensor component is being driven with the drive current and output a first feedback signal representative of the first actual current value. The second current sensor is configured to measure a second actual current value of current that is actually on the second wire while the sensor component is being driven with the drive current and output a second feedback signal representative of the second actual current value. A summing circuit included in the control loop circuit is configured to subtract the first and second feedback signals from the control signal to output an error signal that specifies the gain parameter.

As described herein, the current sensors are oriented with respect to the first and second wires such that any current detected on the wires that is due to external electric fields is effectively canceled out by the summing circuit. This allows the control loop to abstain from reacting to (e.g., by adjusting the gain parameter in response to) current injected by the external electric fields. However, any current detected on the wires that is due to the drive current supplied by the driver is not canceled out by the summing circuit, thereby allowing the control loop circuit to react to (e.g., adjust the gain parameter in response to) current on the wires that is due to the drive current.

Various advantages and benefits are associated with the systems, circuits, and methods described herein. For example, the systems, circuits, and methods described herein may allow a sensing component (or any other suitable load) to be driven over an unshielded twisted pair wire configuration (e.g., an unshielded twisted pair cable). This may allow the cabling between the controller and the sensing component to be relatively light weight, compact, agile, and/or low cost compared to conventional shielded cable configurations. Moreover, the systems, circuits, and methods described herein may mitigate (e.g., eliminate) undesirable current from being driven through a sensing component, which may optimize a performance of the sensing component. These and other advantages and benefits are described herein.

The sensing components referred to herein may be included in any suitable sensing system. For example, the sensing components may be included in a magnetic field measurement system, including systems for magnetoencephalography (MEG).

FIG. 1 shows an exemplary magnetic field measurement system 100 ("system 100"). System 100 is described more fully in U.S. patent application Ser. No. 16/862,879, filed Apr. 30, 2020; and U.S. Provisional Application No. 63/058,616, filed Jul. 30, 2020, which applications are incorporated by reference herein in their entirety. These systems can be used in a magnetically shielded environment which can allow for user movement as described for example in U.S. Provisional Application No. 63/076,015, filed Sep. 9, 2020, which is expressly incorporated herein by reference in its entirety.

As shown, system 100 includes a wearable sensor unit 102 and a controller 104. Wearable sensor unit 102 includes a plurality of magnetometers 106-1 through 106-N (collectively "magnetometers 106") and a magnetic field generator 108. Wearable sensor unit 102 may include additional components (e.g., one or more magnetic field sensors, position sensors, orientation sensors, accelerometers, image recorders, detectors, etc.) as may serve a particular implementation. System 100 may be used in MEG and/or any other application that measures relatively weak magnetic fields.

Wearable sensor unit 102 is configured to be worn by a user (e.g., on a head of the user). In some examples, wearable sensor unit 102 is portable. In other words, wearable sensor unit 102 may be small and light enough to be easily carried by a user and/or worn by the user while the user moves around and/or otherwise performs daily activities.

Any suitable number of magnetometers 106 may be included in wearable sensor unit 102. For example, wearable sensor unit 102 may include an array of nine, sixteen, twenty-five, or any other suitable plurality of magnetometers 106 as may serve a particular implementation.

Magnetometers 106 may each be implemented by any suitable combination of components configured to be sensitive enough to detect a relatively weak magnetic field (e.g., magnetic fields that come from the brain). For example, each magnetometer may include a light source, a vapor cell such as an alkali metal vapor cell (the terms "cell", "gas cell", "vapor cell", and "vapor gas cell" are used interchangeably herein), a heater for the vapor cell, and a photodetector (e.g., a signal photodiode). Examples of suitable light sources include, but are not limited to, a diode laser (such as a vertical-cavity surface-emitting laser (VCSEL), distributed Bragg reflector laser (DBR), or distributed feedback laser (DFB)), light-emitting diode (LED), lamp, or any other suitable light source. In some embodiments, the light source may include two light sources: a pump light source and a probe light source. These magnetometer components, and manners in which they operate to detect magnetic fields, are described in more detail herein, as well as in in U.S. patent application Ser. No. 16/457,655, filed Jun. 28, 2019; U.S. patent application Ser. No. 16/213,980, filed Dec. 7, 2018 (now U.S. patent Ser. No. 10/627,460); U.S. patent application Ser. No. 16/752,393, filed Jan. 24, 2020; U.S. patent application Ser. No. 16/820,131 filed Mar. 16, 2020; U.S. patent application Ser. No. 16/850,444; and U.S. patent application Ser. No. 16/984,752, filed Aug. 4, 2020, which applications are incorporated by reference herein in their entirety.

Magnetic field generator 108 may be implemented by one or more components configured to generate one or more compensation magnetic fields that actively shield magnetometers 106 (including respective vapor cells) from ambient background magnetic fields (e.g., the Earth's magnetic field, magnetic fields generated by nearby magnetic objects such as passing vehicles, electrical devices and/or other field generators within an environment of magnetometers 106, and/or magnetic fields generated by other external sources). For example, magnetic field generator 108 may include one or more coils configured to generate compensation magnetic fields in the Z direction, X direction, and/or Y direction (all directions are with respect to one or more planes within which the magnetic field generator 108 is located). The compensation magnetic fields are configured to cancel out, or substantially reduce, ambient background magnetic fields in a magnetic field sensing region with minimal spatial variability.

Controller 104 is configured to interface with (e.g., control an operation of, receive signals from, etc.) magnetometers 106 and the magnetic field generator 108. Controller 104 may also interface with other components that may be included in wearable sensor unit 102.

In some examples, controller 104 is referred to herein as a "single" controller 104. This means that only one controller is used to interface with all of the components of wearable sensor unit 102. For example, controller 104 may be the only controller that interfaces with magnetometers 106 and magnetic field generator 108. It will be recognized, however, that any number of controllers may interface with components of magnetic field measurement system 100 as may suit a particular implementation.

As shown, controller 104 may be communicatively coupled to each of magnetometers 106 and magnetic field generator 108. For example, FIG. 1 shows that controller 104 is communicatively coupled to magnetometer 106-1 by way of communication link 110-1, to magnetometer 106-2 by way of communication link 110-2, to magnetometer 106-N by way of communication link 110-N, and to magnetic field generator 108 by way of communication link 112. In this configuration, controller 104 may interface with magnetometers 106 by way of communication links 110-1 through 110-N (collectively "communication links 110") and with magnetic field generator 108 by way of communication link 112.

Communication links 110 and communication link 112 may be implemented by any suitable wired connection as may serve a particular implementation. For example, communication links 110 may be implemented by one or more twisted pair cables while communication link 112 may be implemented by one or more coaxial cables. Alternatively, communication links 110 and communication link 112 may both be implemented by one or more twisted pair cables. As described herein, the twisted pair cables may be unshielded.

Controller 104 may be implemented in any suitable manner. For example, controller 104 may be implemented by a field-programmable gate array (FPGA), an application specific integrated circuit (ASIC), a digital signal processor (DSP), a microcontroller, and/or other suitable circuit together with various control circuitry.

In some examples, controller 104 is implemented on one or more printed circuit boards (PCBs) included in a single housing. In cases where controller 104 is implemented on a PCB, the PCB may include various connection interfaces configured to facilitate communication links 110 and 112. For example, the PCB may include one or more twisted pair cable connection interfaces to which one or more twisted pair cables may be connected (e.g., plugged into) and/or one or more coaxial cable connection interfaces to which one or more coaxial cables may be connected (e.g., plugged into).

Figure 2:
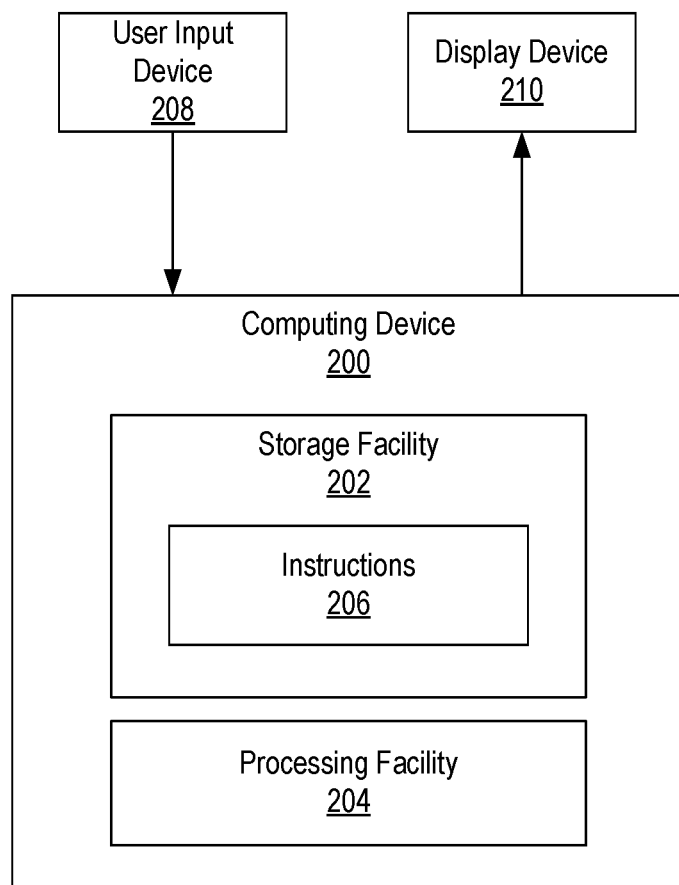
FIG. 2 illustrates an exemplary computing device that may implement a controller of the magnetic field measurement system of FIG. 1.

In some examples, controller 104 may be implemented by or within a computing device. FIG. 2 illustrates an exemplary computing device 200 that may implement controller 104. Computing device 200 may be implemented by a desktop computer, a mobile device, a server, and/or any other single computing device having a single housing for components of the computing device.

As shown, computing device 200 may include, without limitation, a storage facility 202 and a processing facility 204 selectively and communicatively coupled to one another. Facilities 202 and 204 may each include or be implemented by hardware and/or software components (e.g., processors, memories, communication interfaces, instructions stored in memory for execution by the processors, etc.).

Storage facility 202 may maintain (e.g., store) executable data used by processing facility 204 to perform one or more of the operations described herein. For example, storage facility 202 may store instructions 206 that may be executed by processing facility 204 to perform one or more of the operations described herein. Instructions 206 may be implemented by any suitable application, software, code, and/or other executable data instance. Storage facility 202 may also maintain any data received, generated, managed, used, and/or transmitted by processing facility 204.

Processing facility 204 may be configured to perform (e.g., execute instructions 206 stored in storage facility 202 to perform) various operations described herein.

As shown, computing device 200 may be communicatively coupled to a user input device 208 and to a display device 210. User input device 208 may be implemented by a keyboard, a mouse, a touch screen, a track ball, a joystick, a voice recognition system, and/or any other component configured to facilitate providing of user input to computing device 200. Display device 210 may be implemented by a monitor, a screen, a printer, and/or any other device configured to display output provided by computing device 200. In some examples, display device 210 is integrated into a single unit with computing device 200.

Figure 3:
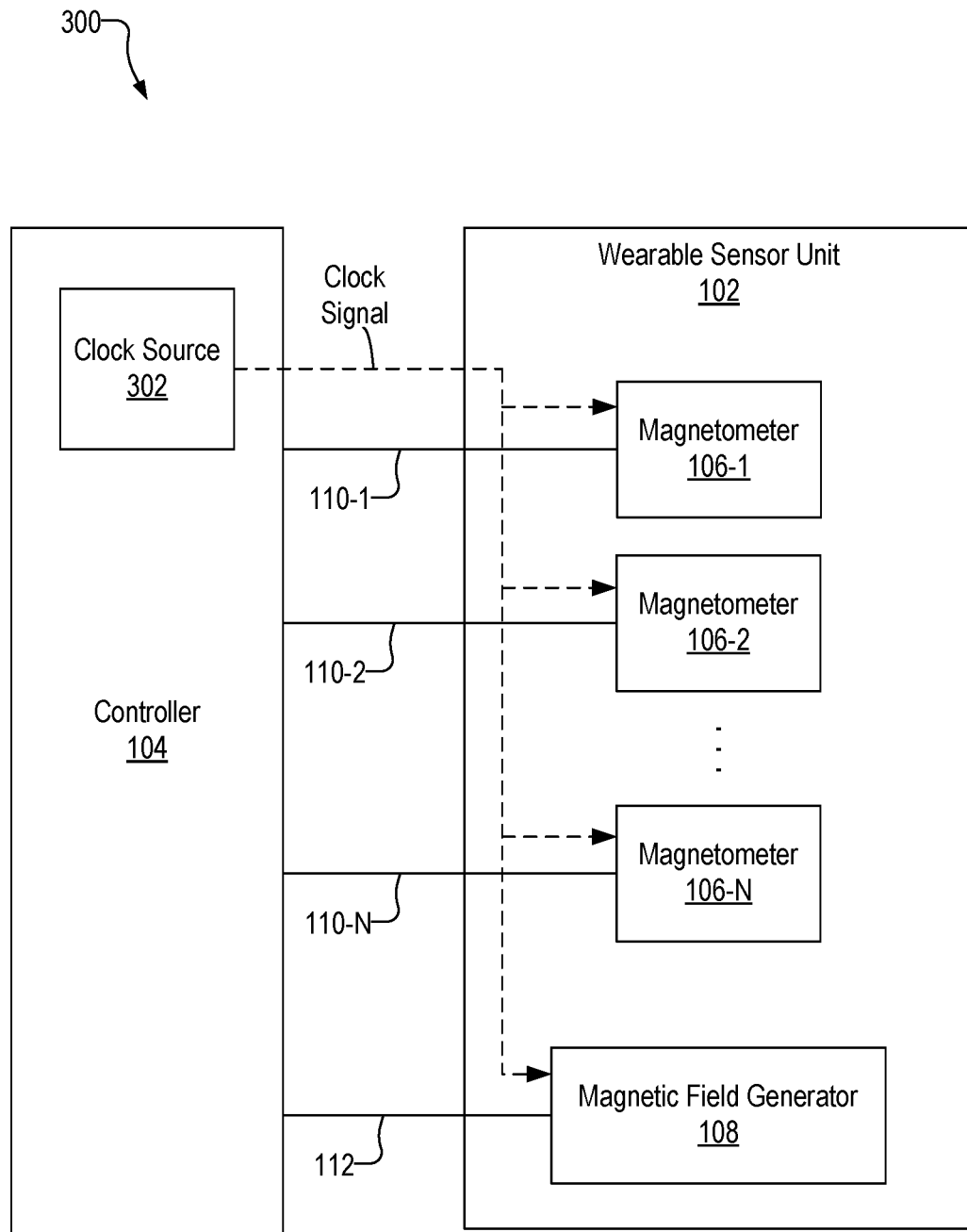
FIG. 3 illustrates an exemplary configuration of the magnetic field measurement system of FIG. 1.

FIG. 3 illustrates an exemplary configuration 300 of system 100 in which controller 104 includes a clock source 302 configured to generate a common clock signal used by controller 104 to interface with the components of wearable sensor unit 102. For example, controller 104 may use the common clock signal to drive or otherwise control various components within each of magnetometers 106 and drive or otherwise control magnetic field generator 108. Use of the common clock signal to interface with magnetometers 106 and magnetic field generator 108 is illustrated in FIG. 3 (and various other figures) by dashed lines interconnecting clock source 302 and magnetometers 106 and magnetic field generator 108.

By using a single common clock signal (as opposed to an array of independent clocks as done in conventional configurations), controller 104 may ensure that communication with magnetometers 106 and magnetic field generator 108 (and, in some implementations, other components within wearable sensor unit 102) is synchronized, thereby reducing or eliminating crosstalk between signals transmitted between controller 104 and wearable sensor unit 102, as well as providing other benefits described herein.

In some implementations, as illustrated in FIGS. 1 and 3, controller 104 is remote from (i.e., not included within) wearable sensor unit 102. For example, in these implementations, controller 104 may be implemented by or included in a standalone computing device not configured to be worn by a user (e.g., computing device 200). The computing device may interface with one or more user input devices (e.g., user input device 208) and one or more display devices (e.g., display device 210). In this manner, a user may provide user input by way of the computing device to control, program, configure, and/or otherwise interface with controller 104. The computing device may present information (e.g., output data generated by wearable sensor unit 102) by way of the one or more display devices.

Figure 4:
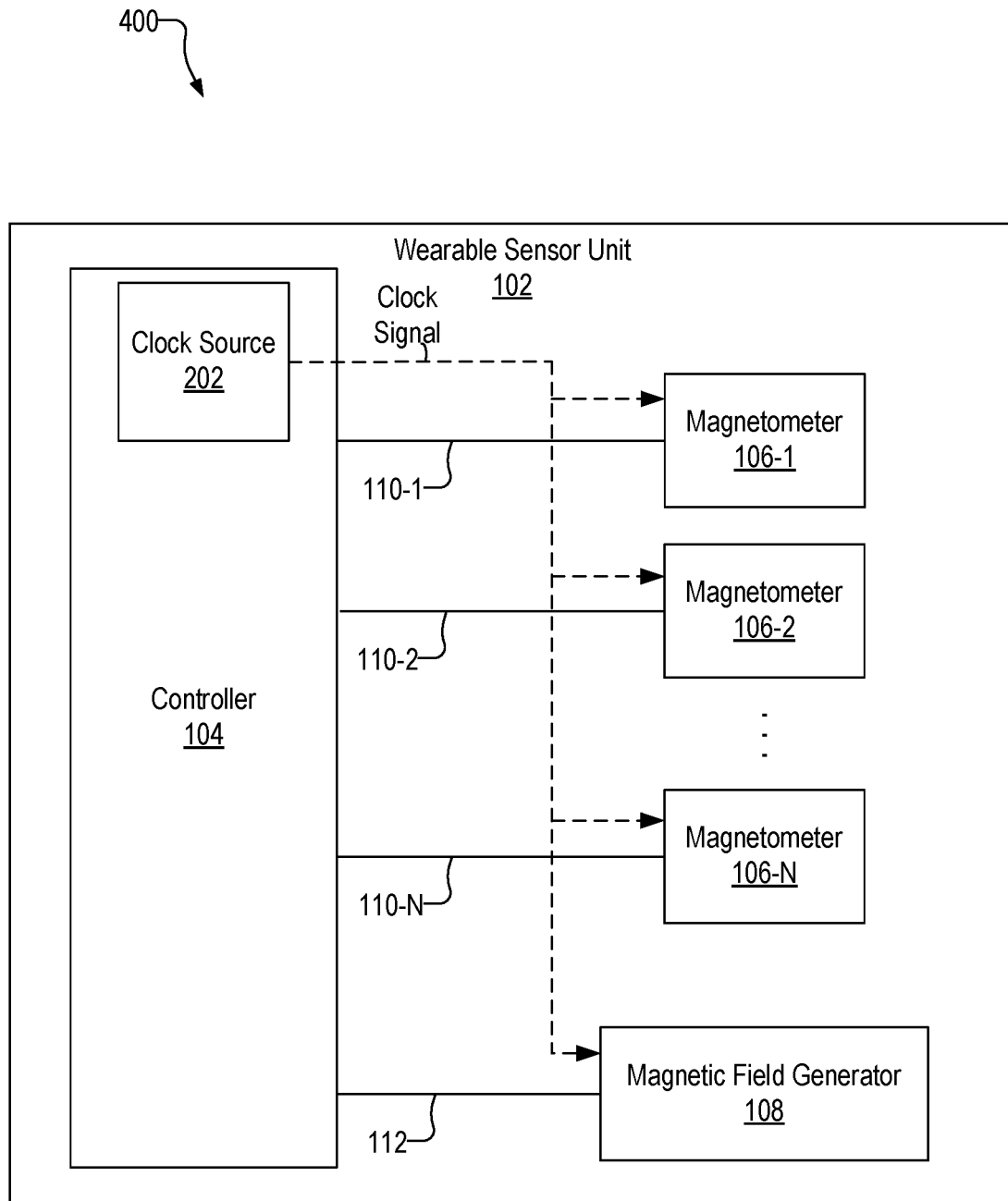
FIG. 4 illustrates another exemplary configuration of the magnetic field measurement system of FIG. 1.

FIG. 4 shows an alternative configuration 400 in which controller 104 is included within wearable sensor unit 102. Configuration 400 may allow a user of wearable sensor unit 102 to travel or otherwise move freely while still wearing wearable sensor unit 102 without having to ensure that wearable sensor unit 102 is connected to a separate non-wearable controller.

In configuration 400, controller 104 may include one or more interfaces (e.g., wired or wireless interfaces) configured to facilitate communication between controller 104 and an external computing device. In this manner, a user may use the external computing device to control, program, configure, or otherwise interface with controller 104. Wearable sensor unit 102 may further include a power supply (not shown) configured to provide operating power to controller 104 and various other components included in wearable sensor unit 102.

As another exemplary configuration, controller 104 may be included in a wearable sensor unit other than wearable sensor unit 102. For example, a magnetic field measurement system may include a first wearable sensor unit and a second wearable sensor unit. A controller included in the first wearable sensor unit may be communicatively coupled to the second wearable senor unit and configured to control both the first and second wearable senor units. To this end, the first and second wearable sensor units may be communicatively coupled by way of any suitable communication link.

As another exemplary configuration, controller 104 may be included in a wearable device configured to be worn by a user and separate from wearable sensor unit 102. For example, controller 104 may be included in a wearable device (e.g., a device that may be worn on the head, on the back (e.g., in a backpack), and/or on the waist (e.g., in a unit configured to clip or strap to a belt of the user) and communicatively coupled to wearable sensor unit 102 by way of any suitable communication link. Examples of this are described herein.

Figure 5:
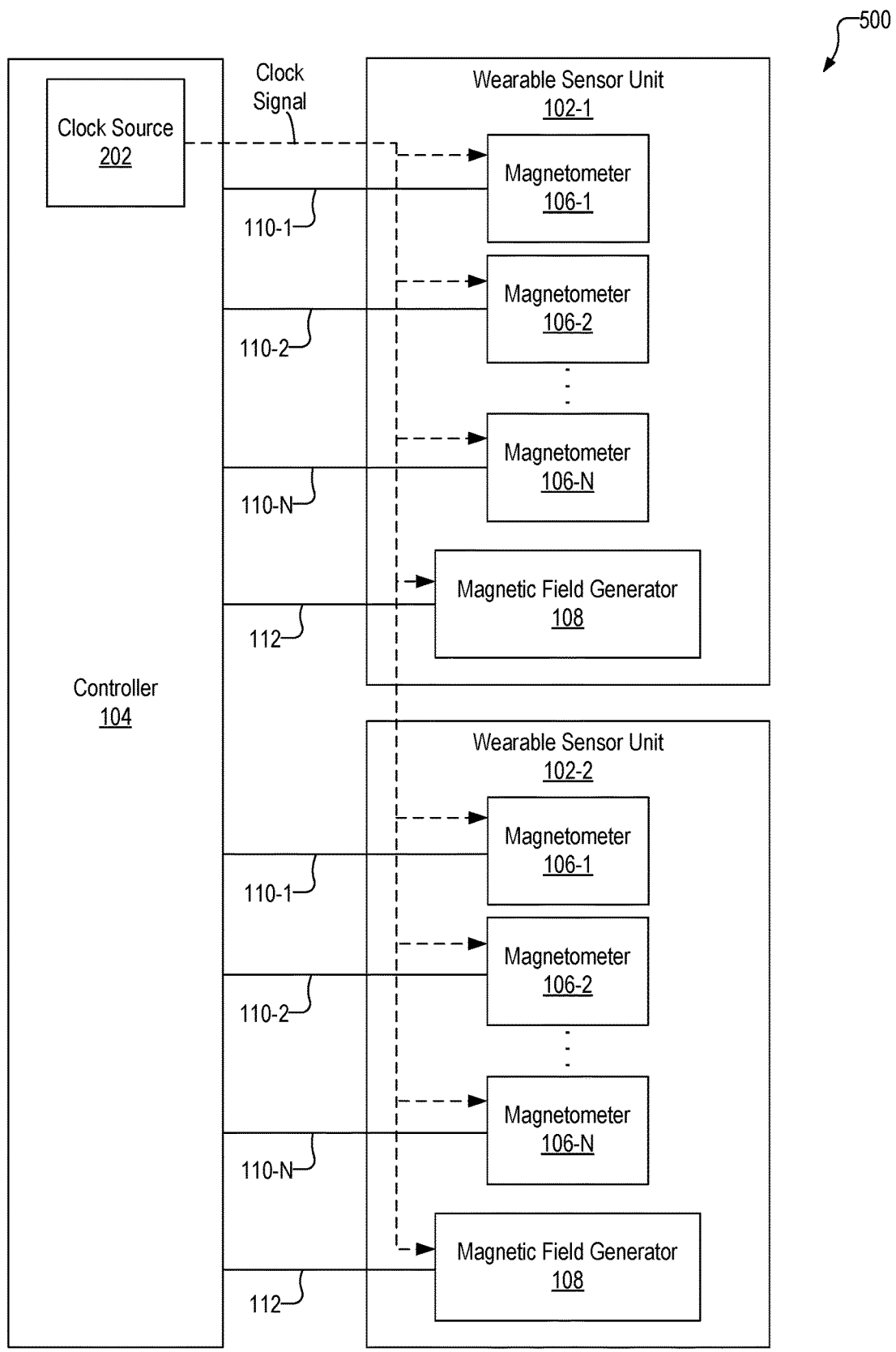
FIG. 5 illustrates yet another exemplary configuration of the magnetic field measurement system of FIG. 1.

FIG. 5 shows an exemplary configuration 500 in which controller 104 is configured to concurrently interface with multiple wearable sensor units (e.g., multiple wearable sensor units configured to be worn concurrently by a user). For example, as shown, controller 104 is communicatively coupled to wearable sensor unit 102-1 and wearable sensor unit 102-2 (collectively "wearable sensor units 102"). As shown, both wearable sensor units 102 include a plurality of magnetometers 106 and a magnetic field generator 108. As shown, controller 104 may interface with magnetometers 106 by way of communication links 110 and with magnetic field generators 108 by way of communication links 112.

As shown, the common clock signal output by clock source 302 is configured to be used by controller 104 to control or otherwise interface with all of the components of both wearable sensor units 102. In this manner, operation of and data output by wearable sensor units 102 may be synchronized.

In the examples described above, controller 104 of system 100 may control or interface with various components of one or more wearable sensor units 102 to measure biological or other magnetic fields. As explained above, a wearable sensor unit 102 may include, in some examples, one or more magnetometers 106 and a magnetic field generator 108. These components will now be described.

Magnetometers 106 may be any suitable magnetometers, such as but not limited to optically pumped magnetometers (OPMs), nitrogen vacancy (NV) diamond sensors, and magnetoresistance sensors. OPMs may operate in a vector mode and/or a scalar mode. In some examples, vector mode OPMs may operate at zero-fields and may utilize a spin exchange relaxation free (SERF) mode to reach femto-Tesla sensitivities.

Figure 6:
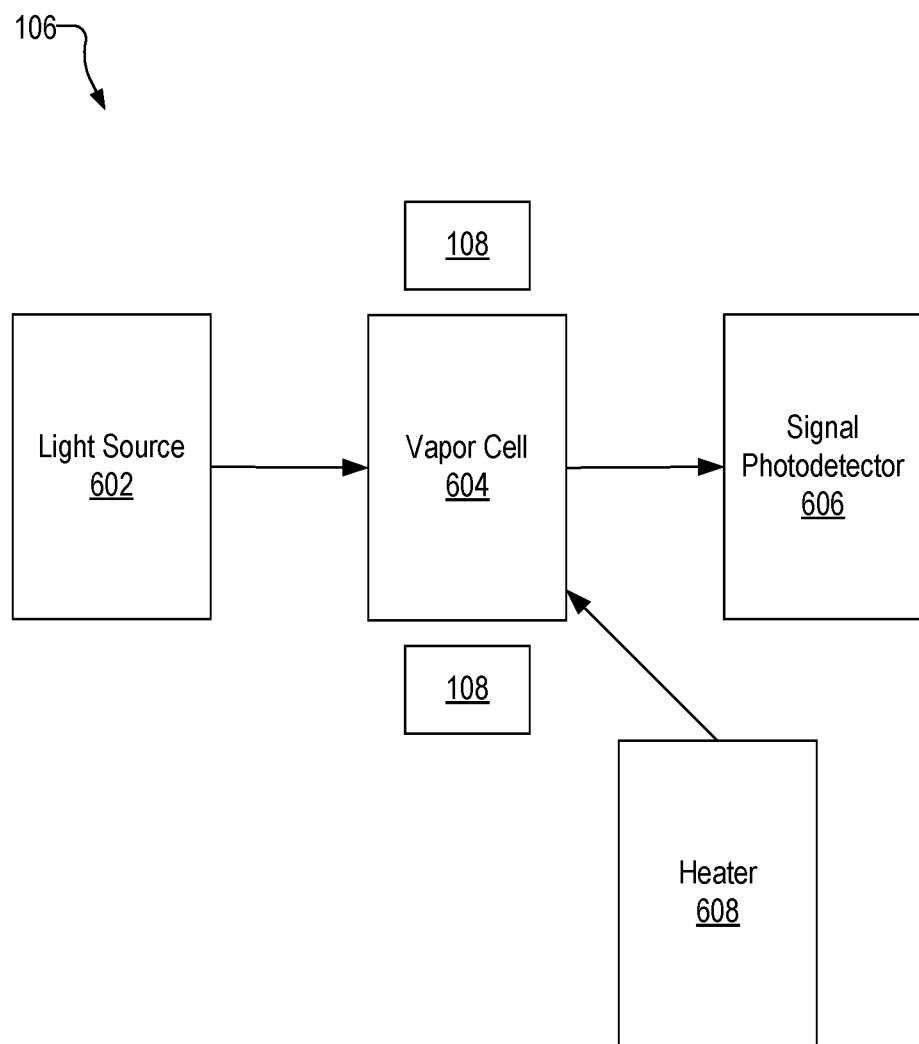
FIG. 6 illustrates a block diagram of an exemplary magnetometer.

FIG. 6 illustrates a block diagram of an exemplary magnetometer 106. As shown, magnetometer 106 is an OPM. Magnetometer 106 includes a light source 602, a vapor cell 604, a signal photodetector 606, and a heater 608. In addition, the magnetic field generator 108 can be positioned around the vapor cell 604. Magnetometer 106 may include additional or alternative components as may suit a particular implementation, such as optics (e.g., lenses, waveplates, collimators, polarizers, and/or objects with reflective surfaces for beam shaping and polarization control and for directing light from light source 602 to vapor cell 604 and to signal photodetector 606) and/or any other suitable components.

Light source 602 is configured to generate and emit light (e.g., laser light) to optically pump alkali metal atoms in vapor cell 604 and to probe vapor cell 604.

Vapor cell 604 contains an alkali metal vapor (e.g., rubidium in natural abundance, isotopically enriched rubidium, potassium, or cesium, or any other suitable alkali metal such as lithium, sodium, potassium, rubidium, cesium, or francium) and, optionally, a quenching gas (e.g., nitrogen) and/or a buffer gas (e.g., nitrogen, helium, neon, or argon). It will be recognized that vapor cell 604 can contain additional or other gases or vapors as may suit a particular implementation. Heater 608 is configured to heat vapor cell 604.

Signal photodetector 606 is configured to detect and measure optical properties (e.g., amplitude, phase, and/or polarization) of light emitted by light source 602 that has passed through vapor cell 604. Examples of suitable signal photodetectors include, but are not limited to, a photodiode, a charge coupled device (CCD) array, a CMOS array, a camera, a photodiode array, a single photon avalanche diode (SPAD) array, an avalanche photodiode (APD) array, and/or any other suitable optical sensor array that can measure a change in transmitted light at the optical wavelengths of interest.

Operation of magnetometer 106 will now be described. Light emitted by light source 602 enters vapor cell 604 where it induces a transparent steady state in the alkali metal vapor. In the transparent steady state the light is allowed to pass through the vapor cell 604 with minimal absorption by the alkali metal vapor and, hence, maximal detection by signal photodetector 606. Magnetic fields generated from a target source (e.g., magnetic fields generated by a user's brain) cause the transparency of the alkali metal vapor to decrease so that less light is detected at signal photodetector 606. The change in light detected at signal photodetector 606 is correlated to magnetic fields generated by the target source.

However, ambient background magnetic fields may interfere with the measurement by magnetometer 106 of magnetic fields generated by a target source. As used herein, the term "ambient background magnetic fields" refers to a magnetic field or magnetic fields associated with (e.g., generated by) sources other than system 100 and the sources of interest (e.g., magnetic fields associated with neural signals from a user's brain). The ambient background magnetic fields can include, for example, the Earth's magnetic field as well as magnetic fields from magnets, electromagnets, electrical devices, and other signal or field generators in the environment other than magnetic field generator 108 that is part of system 100.

Accordingly, wearable sensor unit 102 includes one or more active magnetic field shields (e.g., magnetic field generator 108) and, optionally, one or more passive magnetic field shields. An active magnetic field shield generates, for example, an equal and opposite magnetic vector that cancels out, or substantially reduces, the ambient background magnetic fields. A passive magnetic field shield redirects magnetic fields away from magnetic field sensors (e.g., away from magnetometers 106). Exemplary passive magnetic field shields are described in more detail in U.S. patent application Ser. No. 16/457,655, which is incorporated herein by reference in its entirety.

Figure 7:
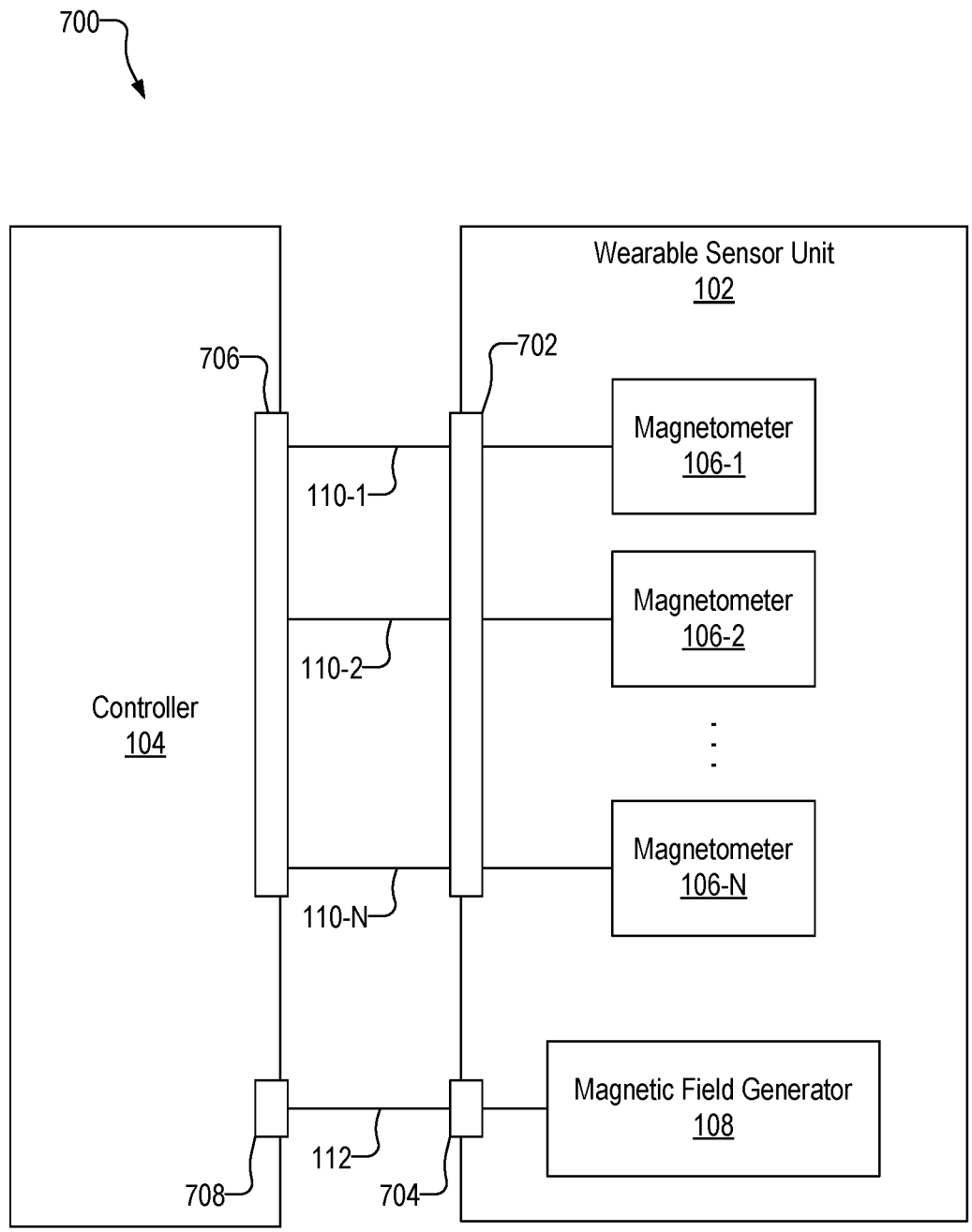
FIG. 7 shows an exemplary configuration in which a wearable sensor unit and a controller each include connection interfaces configured to facilitate wired connections therebetween.

FIG. 7 shows an exemplary configuration 700 in which wearable sensor unit 102 and controller 104 each include connection interfaces configured to facilitate wired connections therebetween. As shown, wearable sensor unit 102 includes a connection interface 702 for magnetometers 106 and a connection interface 704 for magnetic field generator 108. Controller 104 includes a connection interface 706 corresponding to connection interface 702 and a connection interface 708 corresponding to connection interface 704. Connection interfaces 702, 704, 706, and 708 may each be implemented in any suitable manner.

To illustrate, connection interface 702 may be implemented by one or more twisted pair cable interface assemblies electrically connected to one or more components within magnetometers 106, and connection interface 706 may be implemented by one or more twisted pair cable interface assemblies electrically connected to one or more components within controller 104. In this configuration, communication links 110 may be implemented by one or more twisted pair cables each including one or more twisted pairs of wires that are configured to electrically connect specific components of magnetometers 106 and/or other elements of wearable sensor unit 102 with specific components of controller 104. The one or more twisted pair cable interface assemblies of wearable sensor unit 102 and controller 104 may each be configured to connect to a twisted pair cable in any suitable manner.

In this configuration, controller 104 may be configured to interface with one or more components included in magnetometers 106 and/or other elements of wearable sensor unit 102 by transmitting signals to the one or more components over one or more twisted pair cables and/or receiving signals from the one or more components over the one or more twisted pair cables.

Figure 8:
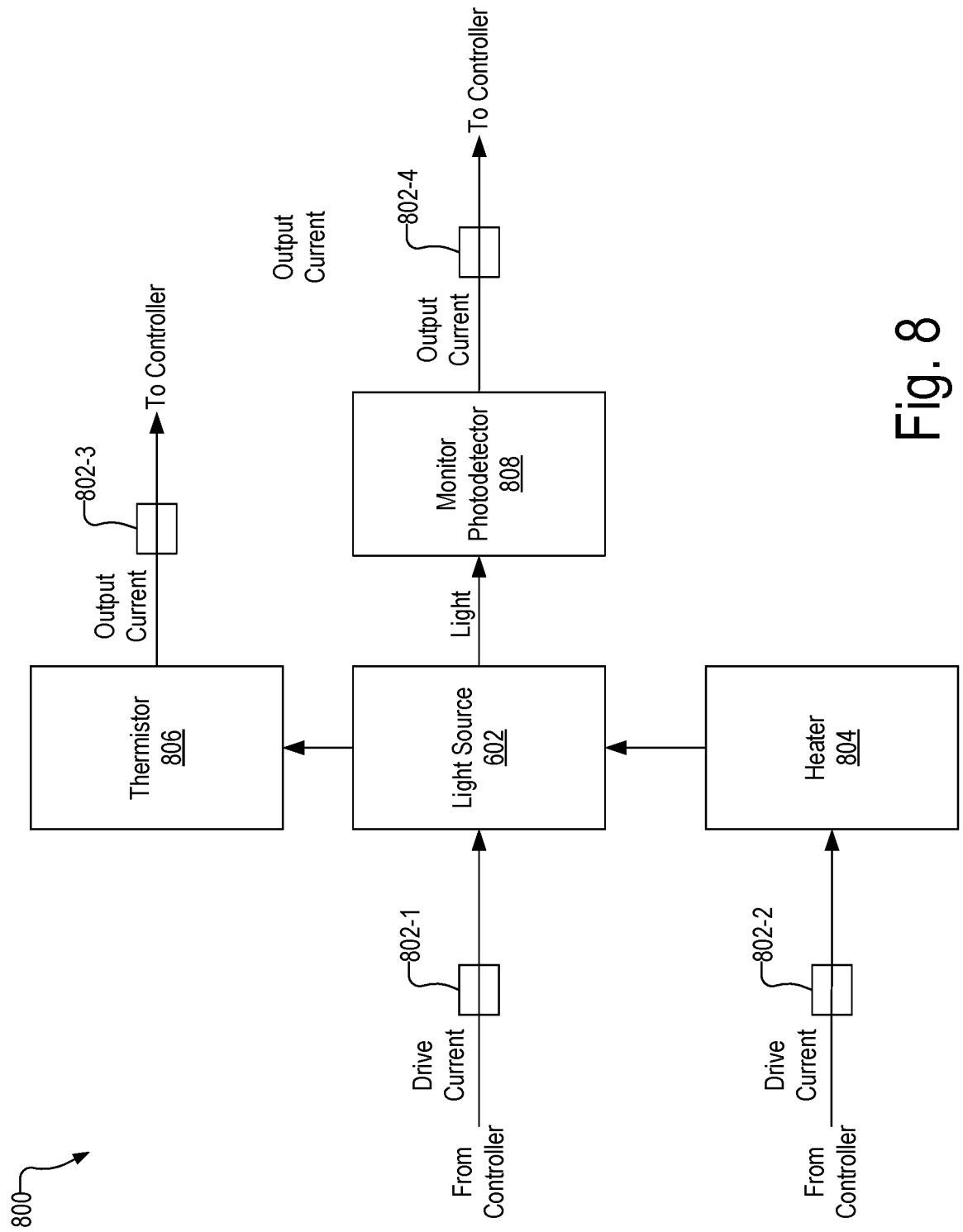
FIG. 8 shows an exemplary configuration in which a controller interfaces with various components of or associated with a particular magnetometer by way of a plurality of twisted pair cable interfaces.

To illustrate, FIG. 8 shows an exemplary configuration 800 in which controller 104 interfaces with various components of or associated with a particular magnetometer 106 by way of a plurality of twisted pair cable interfaces 802 (e.g., twisted pair cable interfaces 802-1 through 802-4) included in wearable sensor unit 102. As shown, twisted pair cable interface 802-1 is electrically connected to an input of light source 602 (described above in connection with FIG. 6), twisted pair cable interface 802-2 is electrically connected to an input of a heater 804 for light source 602, twisted pair cable interface 802-3 is electrically connected to an output of a thermistor 806 for light source 602, and twisted pair cable interface 802-4 is electrically connected to an output of a monitor photodetector 808 for light source 602.

As mentioned, light source 602 is configured to generate and output light that enters and exits (e.g., by passing through) vapor cell 604 (not shown in FIG. 8). To control (e.g., drive) light source 602, controller 104 may supply a drive current to the input of light source 602 by way of twisted pair cable interface 802-1. For example, this drive current may be supplied by controller 104 over a twisted pair of wires included in a twisted pair cable connected to twisted pair cable interface 802-1.

As shown, the light output by light source 602 may be detected by monitor photodetector 808, which is configured to detect the light before the light enters vapor cell 604 and output current representative of the detected light. Controller 104 may use the output of monitor photodetector 808 to monitor and compensate for a behavior of light source 602 in any suitable manner. For example, based on the output of monitor photodetector 808, controller 104 may adjust the drive current provided to light source 602.

Controller 104 may be configured to read an output of monitor photodetector 808 by way of twisted pair cable interface 802-4. For example, controller 104 may receive the current output by monitor photodetector 808 over a twisted pair of wires included in a twisted pair cable connected to twisted pair cable interface 802-4.

Heater 804 may be configured to apply heat to light source 602. To this end, heater 804 may be thermally coupled to light source 602. To control (e.g., drive) heater 804, controller 104 may supply a drive current to the input of heater 804 by way of twisted pair cable interface 802-2. For example, this drive current may be supplied by controller 104 over a twisted pair of wires included in a twisted pair cable connected to twisted pair cable interface 802-2.

Thermistor 806 may be configured to detect the operating temperature of light source 602 and output current representative of the operating temperature. To this end, thermistor 806 may be thermally coupled to light source 602. Controller 104 may be configured to read an output of thermistor 806 by way of twisted pair cable interface 802-3. For example, controller 104 may receive the current output by thermistor 806 over a twisted pair of wires included in a twisted pair cable connected to twisted pair cable interface 802-3. Additionally or alternatively, controller 104 may supply a drive current to thermistor 806 to facilitate functionality of thermistor 806 over a twisted pair of wires.

Heater 804 and thermistor 806 may be used by controller 104 to control an operating temperature of light source 602. For example, heater 804 and thermistor 806 may be used to temperature control light source 602 down to a particular threshold (e.g., within one millikelvin of temperature stability).

Any of the twisted pair cable interfaces 802 shown in FIG. 8 may be used by controller 104 to interface with multiple components within wearable sensor unit 102. For example, twisted pair cable interface 802-1 may be used to supply drive current to all of the light sources 602 included in an array of magnetometers 106. To illustrate, if there are twenty-five light sources 602 included in wearable sensor unit 102, twisted pair cable interface 802-1 may include twenty-five pairs of twisted wire each configured to be used by controller 104 to supply drive current to a different one of the twenty-five light sources 602. Likewise, twisted pair cable interface 802-2 may be used to interface with a plurality of heaters 804, twisted pair cable interface 802-3 may be used to interface with a plurality of thermistors 806, and twisted pair cable interface 802-4 may be used to interface with a plurality of monitor photodiodes 808.

Figure 9:
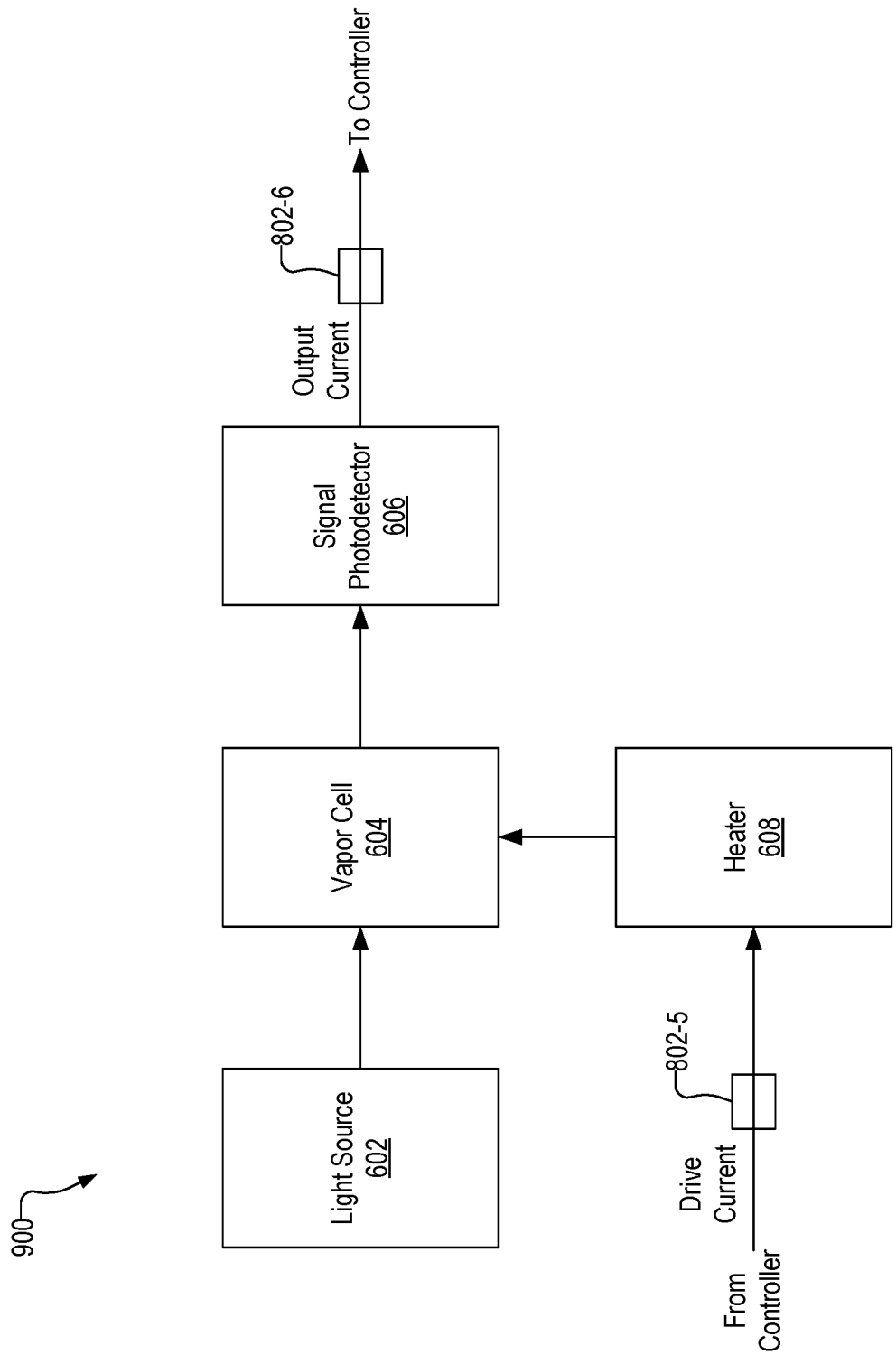
FIG. 9 shows another exemplary configuration in which a controller interfaces with various components of a particular magnetometer by way of a plurality of twisted pair cable interfaces.

FIG. 9 shows another exemplary configuration 900 in which controller 104 interfaces with various components of a particular magnetometer 106 by way of a plurality of twisted pair cable interfaces 802 included in wearable sensor unit 102. FIG. 9 is similar to FIG. 6 in that it depicts light source 602, vapor cell 604, signal photodetector 606, and heater 608. However, FIG. 9 further shows that a twisted pair cable interface 802-5 is electrically connected to an input of heater 608 and a twisted pair cable interface 802-6 is electrically connected to an output of signal photodetector 606.

In configuration 900, controller 104 may control (e.g., drive) heater 608 by supplying a drive current to the input of heater 608 by way of twisted pair cable interface 802-5. For example, this drive current may be supplied by controller 104 over a twisted pair of wires included in a twisted pair cable connected to twisted pair cable interface 802-5. Controller 104 may read an output of signal photodetector 606 by way of twisted pair cable interface 802-6. For example, controller 104 may receive the current output by signal photodetector 606 over a twisted pair of wires included in a twisted pair cable connected to twisted pair cable interface 802-6. As described above, twisted pair cable interfaces 802-5 and 802-6 may in some examples be used to interface with multiple heaters 608 and signal photodetectors 606, respectively.

Figure 10:
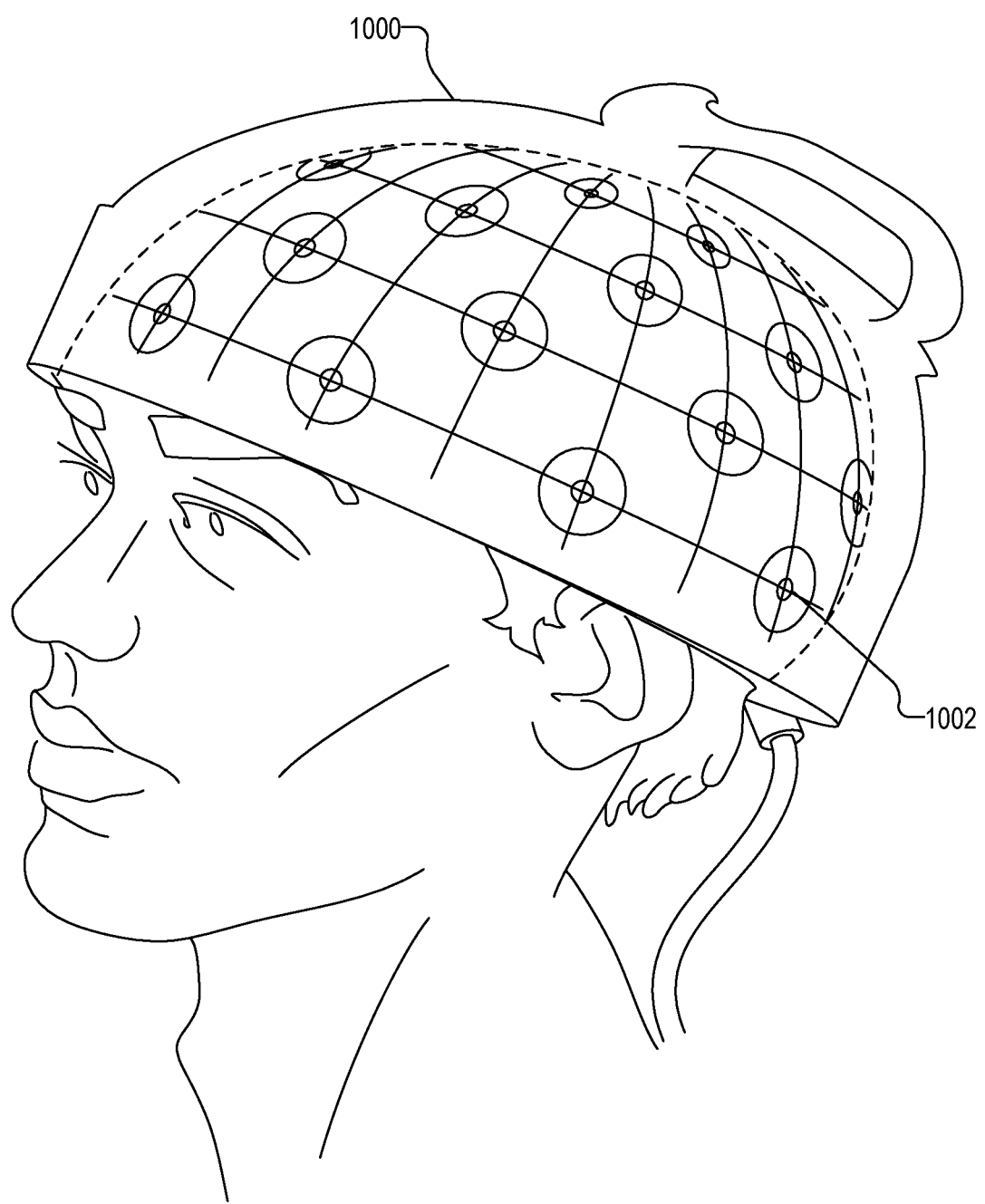
FIG. 10 illustrates a wearable device that includes elements of wearable sensor units described herein.

FIG. 10 illustrates an embodiment of a wearable device 1000 that includes elements of the wearable sensor units described herein. In particular, the wearable device 1000 includes a plurality of optically pumped magnetometer (OPM) modular assemblies 1002, which OPM modular assemblies are enclosed within a housing sized to fit into wearable device 1000 for placement on a head of a user. The OPM modular assembly is designed to enclose the elements of the OPM optics, vapor cell, and detectors in a compact arrangement that can be positioned close to the head of the user. The wearable device 1000 may include an adjustment mechanism to conform with the user's head. These exemplary OPM modular assemblies and systems are described in more detail in U.S. Provisional Patent Application No. 63/058,616, previously incorporated by reference in its entirety. The wearable device 1000 may each also include a controller (e.g., controller 104) and/or be communicatively connected to a controller. In general, wearable device 1000 may be implemented by any suitable headgear configured to be worn by a user.

Figure 11:
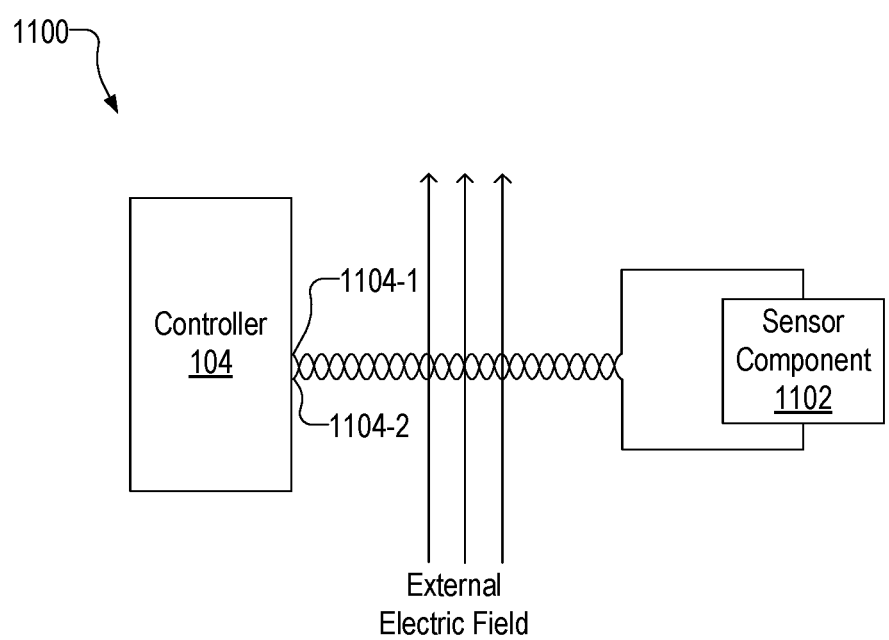
FIG. 11 shows an exemplary configuration in which a controller is configured to drive a sensor component with a drive current over wires in a twisted pair configuration.

FIG. 11 shows an exemplary configuration 1100 in which controller 104 is configured to drive a sensor component 1102 with a drive current over a first wire 1104-1 and a second wire 1104-2 (collectively "wires 1104") included in a twisted pair configuration.

Sensor component 1102 may be implemented by any of the components described herein that are provided with drive current by controller 104. For example, sensor component 1102 may be implemented by any component associated with a magnetometer (e.g., a light source included in the magnetometer, a thermistor configured to detect an operating temperature of the light source, and/or a heater for the light source and/or for a vapor cell of the photodetector). Additionally or alternatively, sensor component 1102 may be implemented by a coil included in a magnetic field generator as described herein.

Sensor component 1102 may alternatively be included in any other type of sensing system (e.g., a non-MEG sensing system). Moreover, while a sensor component 1102 is shown in FIG. 11, the systems, circuits, and methods described herein may additionally or alternatively be used with any suitable load (e.g., an electrical component) that may be driven by remote electronics over a twisted pair configuration.

Wires 1104 may be included in an unshielded cable (e.g., a cable that does not include a common conductive layer). As such, wires 1104 may be relatively light weight, portable, maneuverable, and/or low cost.

As shown, an external electric field may be present while controller 104 drives sensor component 1102 with drive current. The external electric field may be generated by a number of different sources, examples of which are provided herein. In some instances, the external electric field may cause undesirable current (also referred to as noise) to capacitively couple onto wires 1104. This injected current may, if not counteracted, adversely affect the quality of the current that is driven through the sensor component 1102.

Figure 12:
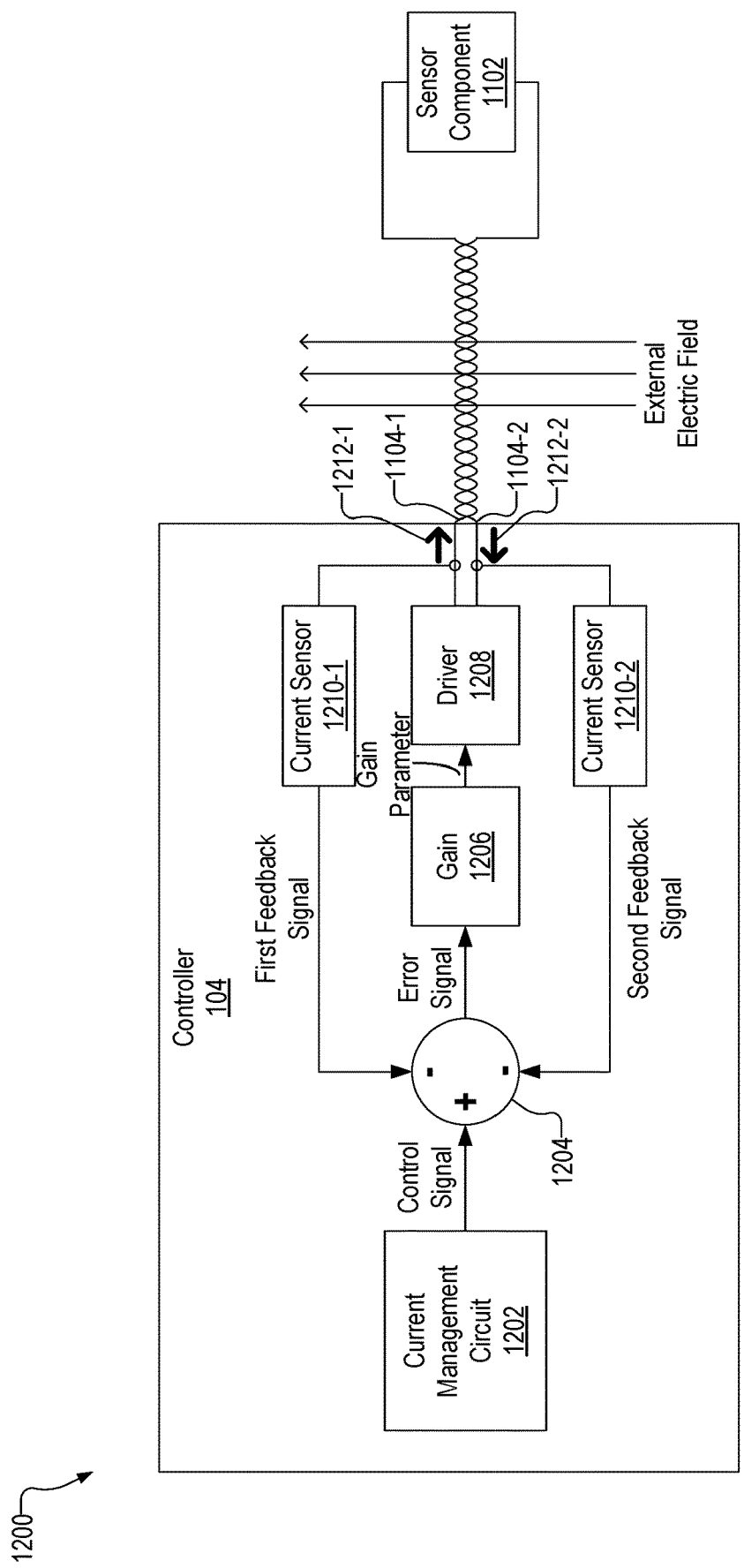
FIG. 12 shows an exemplary configuration of a controller that is configured to mitigate an effect of current injected onto wires by an external electric field.

FIG. 12 shows an exemplary configuration 1200 of controller 104 that is configured to mitigate the effect of current injected onto wires 1104 by an external electric field. As shown, configuration 1200 includes a current management circuit 1202, a summing circuit 1204, a gain block 1206, a driver 1208, and first and second current sensors 1210-1 and 1210-2 (collectively "current sensors 1210").

Current management circuit 1202 may be implemented by any suitable circuit (e.g., a processor) configured to generate and output a control signal. The control signal is representative of a target current value for drive current that is to be applied to sensor component 1102. Current management circuit 1202 may generate the control signal in response to user input (e.g., user input that specifies the target current value). Additionally or alternatively, current management circuit 1202 may generate the control signal automatically based on one or more factors as may serve a particular implementation. In some examples, the control signal is a voltage signal.

Driver 1208 is conductively coupled to wires 1104 and is configured to drive sensor component 1102 with a drive current over wires 1104 in accordance with a gain parameter output by gain block 1206. Driver 1208 and gain block 1206 may be implemented in any suitable manner. For example, driver 1208 and gain block 1206 may be implemented by any suitable amplifier circuit.

The current output by driver 1208 is intended to cause drive current having the target current value to flow through sensor component 1102. However, due to component variations, system irregularities, environmental factors, etc., the actual current value of actual current driven through sensor component 1102 may not exactly match the target current value. As such, a control loop circuit that includes summing circuit 1204, gain block 1206, and current sensors 1210 may be used in combination with driver 1208 to dynamically adjust the current output by driver 1208. This current adjustment may be configured to reduce the difference between the target current value and the actual current value (e.g., by making the target current value and the actual current value match).

To this end, current sensor 1210-1 is configured to measure a first actual current value of current that is actually on wire 1104-1 while sensor component 1102 is being driven with the drive current, and current sensor 1210-2 is configured to measure a second actual current value of current that is actually on wire 1104-2 while sensor component 1102 is being driven with the drive current. Current sensor 1210-1 is further configured to output a first feedback signal representative of the first actual current value, and current sensor 1210-2 is further configured to output a second feedback signal representative of the second actual current value. Both feedback signals may be voltage signals, for example.

As shown, the first and second feedback signals are both input into summing circuit 1204, which also receives the control signal from current management circuit 1202. As shown, summing circuit 1204 is configured to subtract the first and second feedback signals from the control signal to output an error signal. The error signal is input into gain block 1206, which generates (e.g., adjust) the gain parameter based on the error signal.

As such, the control loop circuit shown in FIG. 12 is configured to receive the control signal and adjust the gain parameter based on a difference between the target current value and an actual current value of current that is actually being driven through sensor component 1102. This adjustment is configured to reduce the difference between the target current value and the actual current value.

However, the control loop circuit is also configured to abstain from adjusting the gain parameter based on current capacitively coupled onto the first and second wires by an external electric field. This is in part due to the orientation of current sensors 1210 with respect to wires 1104. In particular, current sensors 1210 are oriented opposite one another with respect to wires 1104.

To illustrate, in the example of FIG. 12, current sensor 1210-1 is oriented in a first direction represented by arrow 1212-1 and current sensor 1210-2 is oriented in a second direction opposite the first direction, as represented by arrow 1212-2.

With this orientation, a drive current component of the first and second actual current values (i.e., a portion of the current detected by current sensors 1210 that is caused by the drive current output by driver 1208) are either both positive or both negative. Both of these values are subtracted from the control signal, which causes the control loop circuit to respond to differences between the drive current and the actual current flowing through sensing component 1102 (e.g., by adjusting the gain parameter).

In contrast, the injected current on wires 1104 due to the external electric field are measured as having opposite signs (e.g., negative and positive) due to the opposite orientations of current sensors 1210. For example, an injected current component of the first actual current value (i.e., a component representative of current caused by the current capacitively coupled onto wire 1104-1) may have a positive sign, while an injected current component of the second actual current value (i.e., a component representative of current caused by the current capacitively coupled onto wire 1104-2) may have a negative sign (or vice versa). As such, these injected current components are rejected by summing circuit 1204 and do not affect the error signal output by summing circuit 1204. Consequently, the control loop circuitry does not respond to the injected current, thereby preventing the injected current from degrading the quality of the drive current that flows through sensor component 1102.

Figure 13:
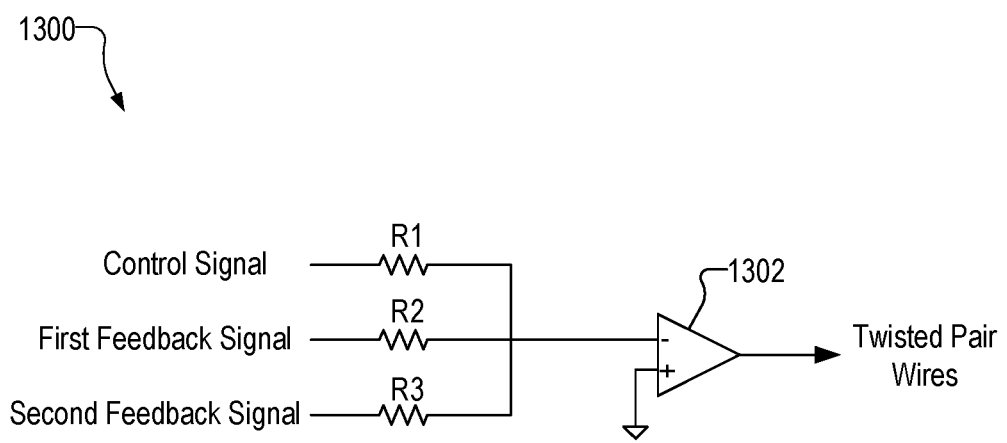
FIG. 13 shows an illustrative summing amplifier circuit.

In some examples, summing circuit 1204, gain block 1206, and driver 1208 are implemented by a summing amplifier circuit. For example, FIG. 13 shows an illustrative summing amplifier circuit 1300. Summing amplifier circuit 1300 includes an operational amplifier 1302 with resistors R1 through R3 connected in parallel to an inverting input of operational amplifier 1302. The non-inverting input of operational amplifier 1302 is connected to ground. Input terminals of resistors R1 through R3 are connected to the control signal, the first feedback signal, and the second feedback signal, as shown.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 14:
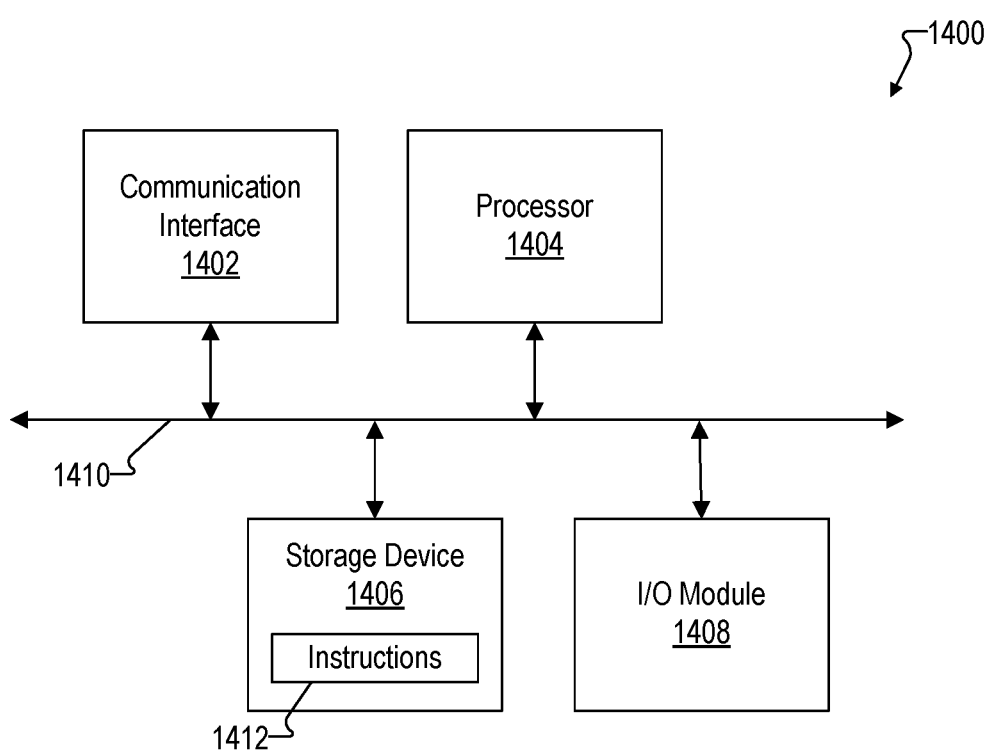
FIG. 14 illustrates an exemplary computing device.

FIG. 14 illustrates an exemplary computing device 1400 that may be specifically configured to perform one or more of the processes described herein. Any of the systems, units, computing devices, and/or other components described herein may be implemented by computing device 1400.

As shown in FIG. 14, computing device 1400 may include a communication interface 1402, a processor 1404, a storage device 1406, and an input/output ("I/O") module 1408 communicatively connected one to another via a communication infrastructure 1410. While an exemplary computing device 1400 is shown in FIG. 14, the components illustrated in FIG. 14 are not intended to be limiting. Additional or alternative components may be used in other embodiments. Components of computing device 1400 shown in FIG. 14 will now be described in additional detail.

Communication interface 1402 may be configured to communicate with one or more computing devices. Examples of communication interface 1402 include, without limitation, a wired network interface (such as a network interface card), a wireless network interface (such as a wireless network interface card), a modem, an audio/video connection, and any other suitable interface.

Processor 1404 generally represents any type or form of processing unit capable of processing data and/or interpreting, executing, and/or directing execution of one or more of the instructions, processes, and/or operations described herein. Processor 1404 may perform operations by executing computer-executable instructions 1412 (e.g., an application, software, code, and/or other executable data instance) stored in storage device 1406.

Storage device 1406 may include one or more data storage media, devices, or configurations and may employ any type, form, and combination of data storage media and/or device. For example, storage device 1406 may include, but is not limited to, any combination of the non-volatile media and/or volatile media described herein. Electronic data, including data described herein, may be temporarily and/or permanently stored in storage device 1406. For example, data representative of computer-executable instructions 1412 configured to direct processor 1404 to perform any of the operations described herein may be stored within storage device 1406. In some examples, data may be arranged in one or more databases residing within storage device 1406.

I/O module 1408 may include one or more I/O modules configured to receive user input and provide user output. I/O module 1408 may include any hardware, firmware, software, or combination thereof supportive of input and output capabilities. For example, I/O module 1408 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1408 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1408 is configured to provide graphical data to a display for presentation to a user. The graphical data may be representative of one or more graphical user interfaces and/or any other graphical content as may serve a particular implementation.

In some examples, any of the systems, computing devices, processors, controllers, and/or other components described herein may be implemented by computing device 1400.

Figure 15:
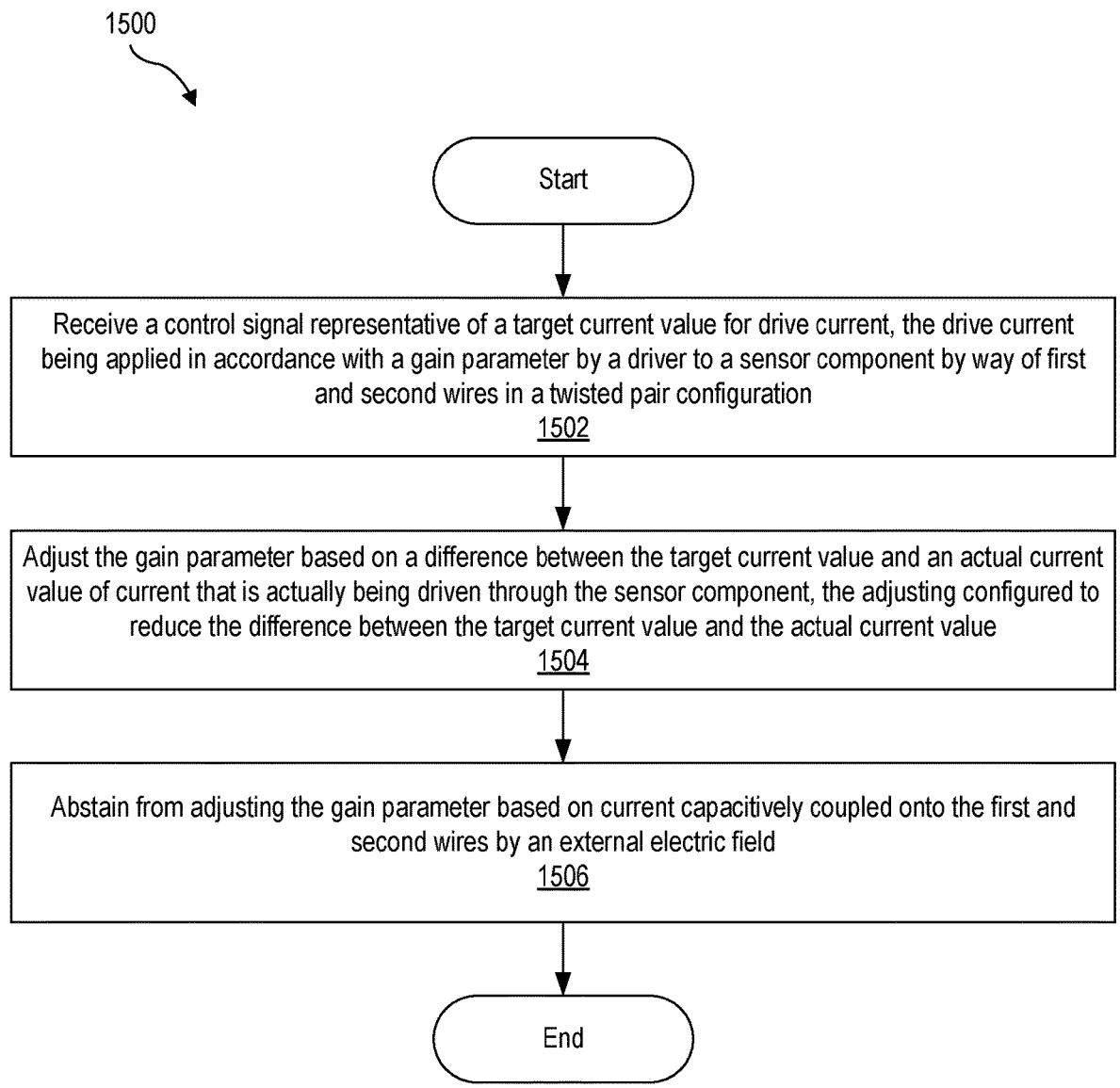
FIG. 15 illustrates an exemplary method.

FIG. 15 illustrates an exemplary method 1500 that may be performed by any of the control loop circuits described herein. While FIG. 15 illustrates exemplary operations according to one embodiment, other embodiments may omit, add to, reorder, and/or modify any of the operations shown in FIG. 15. The operations shown in FIG. 15 may be performed in any of the ways described herein.

At operation 1502, a control loop circuit receives a control signal representative of a target current value for drive current, the drive current being applied in accordance with a gain parameter by a driver to a sensor component by way of first and second wires in a twisted pair configuration.

At operation 1504, the control loop circuit adjusts the gain parameter based on a difference between the target current value and an actual current value of current that is actually being driven through the sensor component, the adjusting configured to reduce the difference between the target current value and the actual current value.

At operation 1506, the control loop circuit abstains from adjusting the gain parameter based on current capacitively coupled onto the first and second wires by an external electric field.

An illustrative system includes a sensor component and a controller conductively coupled to the sensor component by way of a first wire and a second wire in a twisted pair configuration. The controller includes a driver configured to drive the sensor component by way of the first and second wires with a drive current in accordance with a gain parameter, and a control loop circuit configured to receive a control signal representative of a target current value for the drive current, adjust the gain parameter based on a difference between the target current value and an actual current value of current that is actually being driven through the sensor component, the adjusting configured to reduce the difference between the target current value and the actual current value, and abstain from adjusting the gain parameter based on current capacitively coupled onto the first and second wires by an external electric field.

Another illustrative system includes a sensor component, a controller, and an unshielded cable comprising a first wire and a second wire in a twisted pair configuration that conductively couple the controller to the sensor component. The controller includes a driver configured to drive the sensor component by way of the first and second wires with a drive current in accordance with a gain parameter, and a control loop circuit configured to receive a control signal representative of a target current value for the drive current, adjust the gain parameter based on a difference between the target current value and an actual current value of current that is actually being driven through the sensor component, the adjusting configured to reduce the difference between the target current value and the actual current value, and abstain from adjusting the gain parameter based on current capacitively coupled onto the first and second wires by an external electric field.

An illustrative magnetic field measurement system includes a wearable sensor unit configured to be worn by a user and used to detect a magnetic field generated within the user, a sensor component included in the wearable sensor unit, and a controller remote from the wearable sensor unit and conductively coupled to the sensor component by way of a first wire and a second wire in a twisted pair configuration. The controller includes a driver configured to drive the sensor component by way of the first and second wires with a drive current in accordance with a gain parameter, and a control loop circuit configured to receive a control signal representative of a target current value for the drive current, adjust the gain parameter based on a difference between the target current value and an actual current value of current that is actually being driven through the sensor component, the adjusting configured to reduce the difference between the target current value and the actual current value, and abstain from adjusting the gain parameter based on current capacitively coupled onto the first and second wires by an external electric field.

An illustrative apparatus includes a driver conductively coupled to a load by way of a first wire and a second wire in a twisted pair configuration and configured to drive the load with a drive current in accordance with a gain parameter and a control loop circuit. The control loop circuit is configured to receive a control signal representative of a target current value for the drive current, adjust the gain parameter based on a difference between the target current value and an actual current value of current that is actually being driven through the load, the adjusting configured to reduce the difference between the target current value and the actual current value, and abstain from adjusting the gain parameter based on current capacitively coupled onto the first and second wires by an external electric field.

An illustrative apparatus includes a driver conductively coupled to a sensor component by way of a first wire and a second wire in a twisted pair configuration and configured to drive the sensor component with a drive current in accordance with a gain parameter; a first current sensor configured to: measure a first actual current value of current that is actually on the first wire while the sensor component is being driven with the drive current, and output a first feedback signal representative of the first actual current value; a second current sensor configured to: measure a second actual current value of current that is actually on the second wire while the sensor component is being driven with the drive current, and output a second feedback signal representative of the second actual current value; and a summing circuit configured to: receive a control signal representative of a target current value for the drive current, and subtract the first and second feedback signals from the control signal to output an error signal that specifies the gain parameter.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
    a sensor component; and
    a controller conductively coupled to the sensor component by way of a first wire and a second wire in a twisted pair configuration, the controller comprising:
        a driver configured to drive the sensor component by way of the first and second wires with a drive current in accordance with a gain parameter specified by an error signal output by a summing circuit, and
        a control loop circuit configured to
            receive a control signal representative of a target current value for the drive current,
            adjust the gain parameter based on a difference between the target current value and an actual current value of current that is actually being driven through the sensor component, the adjusting configured to reduce the difference between the target current value and the actual current value, and
            abstain from adjusting the gain parameter based on current capacitively coupled onto the first and second wires by an external electric field;
    wherein the control loop circuit comprises:
    a first current sensor configured to
        measure a first actual current value of current that is actually on the first wire while the sensor component is being driven with the drive current, and
        output a first feedback signal representative of the first actual current value;

a second current sensor configured to
measure a second actual current value of current that is actually on the second wire while the sensor component is being driven with the drive current, and output a second feedback signal representative of the second actual current value; and
wherein the summing circuit is configured to subtract the first and second feedback signals from the control signal to output the error signal that specifies the gain parameter.

2. The system of claim 1, wherein an orientation of the first current sensor with respect to the first wire is opposite an orientation of the second current sensor with respect to the second wire such that:
a drive current component of the first actual current value and a drive current component of the second actual current value are either both positive or both negative, the drive current components caused by the drive current output by the driver; and
an injected current component of the first actual current value has a first sign and an injected current component of the second actual current value has a second sign opposite the first sign, the injected current components caused by the current capacitively coupled onto the first and second wires by the external electric field.

3. The system of claim 1, wherein the control signal, the first feedback signal, and the second feedback signal are voltage signals.

4. The system of claim 1, further comprising:
a wearable sensor unit configured to be worn by a user, the wearable sensor unit including a magnetometer configured to detect a magnetic field generated within the user;
wherein the sensor component is included in the wearable sensor unit and associated with the magnetometer.

5. The system of claim 4, wherein the sensor component comprises a light source included in the magnetometer.

6. The system of claim 5, wherein the sensor component comprises a thermistor configured to detect an operating temperature of the light source.

7. The system of claim 6, wherein the sensor component comprises a heater for the light source.

8. The system of claim 4, wherein the sensor component comprises a heater for a vapor cell of the magnetometer.

9. The system of claim 4, wherein:
the wearable sensor unit further includes a magnetic field generator configured to generate a compensation magnetic field configured to actively shield the magnetometer from ambient background magnetic fields; and
the sensor component comprises one or more coils included in the magnetic field generator.

10. The system of claim 4, wherein the controller is implemented by a computing device not configured to be worn by the user.

11. The system of claim 4, wherein the controller is included in a wearable device configured to be worn by the user and separate from the wearable sensor unit.

12. The system of claim 1, wherein the controller further comprises a drive current management circuit configured to generate the control signal and output the control signal to the control loop circuit.

13. The system of claim 1, wherein the first and second wires in the twisted pair configuration are included in an unshielded cable.

14. A system comprising:
a sensor component;
a controller; and
an unshielded cable comprising a first wire and a second wire in a twisted pair configuration that conductively couple the controller to the sensor component;
wherein the controller comprises:
a driver configured to drive the sensor component by way of the first and second wires with a drive current in accordance with a gain parameter specified by an error signal output by a summing circuit, and
a control loop circuit configured to
receive a control signal representative of a target current value for the drive current,
adjust the gain parameter based on a difference between the target current value and an actual current value of current that is actually being driven through the sensor component, the adjusting configured to reduce the difference between the target current value and the actual current value, and
abstain from adjusting the gain parameter based on current capacitively coupled onto the first and second wires by an external electric field;
wherein the control loop circuit comprises:
a first current sensor configured to
measure a first actual current value of current that is actually on the first wire while the sensor component is being driven with the drive current, and
output a first feedback signal representative of the first actual current value;
a second current sensor configured to
measure a second actual current value of current that is actually on the second wire while the sensor component is being driven with the drive current, and
output a second feedback signal representative of the second actual current value; and
wherein the summing circuit is configured to subtract the first and second feedback signals from the control signal to output the error signal that specifies the gain parameter.

15. The system of claim 14, wherein an orientation of the first current sensor with respect to the first wire is opposite an orientation of the second current sensor with respect to the second wire such that:
a drive current component of the first actual current value and a drive current component of the second actual current value are either both positive or both negative, the drive current components caused by the drive current output by the driver; and
an injected current component of the first actual current value has a first sign and an injected current component of the second actual current value has a second sign opposite the first sign, the injected current components caused by the current capacitively coupled onto the first and second wires by the external electric field.

16. A magnetic field measurement system comprising:
a wearable sensor unit configured to be worn by a user and used to detect a magnetic field generated within the user;
a sensor component included in the wearable sensor unit; and
a controller remote from the wearable sensor unit and conductively coupled to the sensor component by way of a first wire and a second wire in a twisted pair configuration, the controller comprising:
a driver configured to drive the sensor component by way of the first and second wires with a drive current in accordance with a gain parameter specified by an error signal output by a summing circuit, and a control loop circuit configured to
receive a control signal representative of a target current value for the drive current,
adjust the gain parameter based on a difference between the target current value and an actual current value of current that is actually being driven through the sensor component, the adjusting configured to reduce the difference between the target current value and the actual current value, and
abstain from adjusting the gain parameter based on current capacitively coupled onto the first and second wires by an external electric field;
wherein the control loop circuit comprises:
a first current sensor configured to
measure a first actual current value of current that is actually on the first wire while the sensor component is being driven with the drive current, and
output a first feedback signal representative of the first actual current value;
a second current sensor configured to
measure a second actual current value of current that is actually on the second wire while the sensor component is being driven with the drive current, and
output a second feedback signal representative of the second actual current value; and
wherein the summing circuit is configured to subtract the first and second feedback signals from the control signal to output the error signal that specifies the gain parameter.

17. The magnetic field measurement system of claim 16, wherein an orientation of the first current sensor with respect to the first wire is opposite an orientation of the second current sensor with respect to the second wire such that:
a drive current component of the first actual current value and a drive current component of the second actual current value are either both positive or both negative, the drive current components caused by the drive current output by the driver; and
an injected current component of the first actual current value has a first sign and an injected current component of the second actual current value has a second sign opposite the first sign, the injected current components caused by
the current capacitively coupled onto the first and second wires by the external electric field.

18. An apparatus comprising:
a driver conductively coupled to a load by way of a first wire and a second wire in a twisted pair configuration and configured to drive the load with a drive current in accordance with a gain parameter specified by an error signal output by a summing circuit; and
a control loop circuit configured to
receive a control signal representative of a target current value for the drive current,
adjust the gain parameter based on a difference between the target current value and an actual current value of current that is actually being driven through the load, the adjusting configured to reduce the difference between the target current value and the actual current value, and
abstain from adjusting the gain parameter based on current capacitively coupled onto the first and second wires by an external electric field;
wherein the control loop circuit comprises:
a first current sensor configured to
measure a first actual current value of current that is actually on the first wire while the load is being driven with the drive current, and
output a first feedback signal representative of the first actual current value;
a second current sensor configured to
measure a second actual current value of current that is actually on the second wire while the load is being driven with the drive current, and
output a second feedback signal representative of the second actual current value; and
wherein the summing circuit is configured to subtract the first and second feedback signals from the control signal to output the error signal that specifies the gain parameter.

19. The apparatus of claim 18, further comprising a drive current management circuit configured to generate the control signal and output the control signal to the control loop circuit.

20. The apparatus of claim 18, wherein an orientation of the first current sensor with respect to the first wire is opposite an orientation of the second current sensor with respect to the second wire such that:
a drive current component of the first actual current value and a drive current component of the second actual current value are either both positive or both negative, the drive current components caused by the drive current output by the driver; and
an injected current component of the first actual current value has a first sign and an injected current component of the second actual current value has a second sign opposite the first sign, the injected current components caused by the current capacitively coupled onto the first and second wires by the external electric field.

21. An apparatus comprising:
a driver conductively coupled to a sensor component by way of a first wire and a second wire in a twisted pair configuration and configured to drive the sensor component with a drive current in accordance with a gain parameter specified by an error signal;
a first current sensor configured to:
measure a first actual current value of current that is actually on the first wire while the sensor component is being driven with the drive current, and
output a first feedback signal representative of the first actual current value;
a second current sensor configured to:
measure a second actual current value of current that is actually on the second wire while the sensor component is being driven with the drive current, and
output a second feedback signal representative of the second actual current value; and
a summing circuit configured to:
receive a control signal representative of a target current value for the drive current, and
subtract the first and second feedback signals from the control signal to output the error signal that specifies the gain parameter.

22. The apparatus of claim 21, wherein an orientation of the first current sensor with respect to the first wire is opposite an orientation of the second current sensor with respect to the second wire such that:
a drive current component of the first actual current value and a drive current component of the second actual current value are either both positive or both negative, the drive current components caused by the drive current output by the driver; and an injected current component of the first actual current value has a first sign and an injected current component of the second actual current value has a second sign opposite the first sign, the injected current components caused by current capacitively coupled onto the first and second wires by an external electric field.

* * * * *